US012714765B2

(12) United States Patent
Pei et al.

(10) Patent No.: US 12,714,765 B2
(45) Date of Patent: Aug. 25, 2026

(54) REVERSIBLE BIOADHESIVE

(71) Applicant: The Regents of the University of California, Oakland, CA (US)

(72) Inventors: Qibing Pei, Los Angeles, CA (US); Meng Gao, Los Angeles, CA (US); Hanxiang Wu, Los Angeles, CA (US); Zhixin Xie, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 184 days.

(21) Appl. No.: 18/263,315

(22) PCT Filed: Jan. 31, 2022

(86) PCT No.: PCT/US2022/014549

§ 371 (c)(1),
(2) Date: Jul. 27, 2023

(87) PCT Pub. No.: WO2022/165327

PCT Pub. Date: Aug. 4, 2022

(65) Prior Publication Data

US 2024/0100218 A1 Mar. 28, 2024

Related U.S. Application Data

(60) Provisional application No. 63/143,163, filed on Jan. 29, 2021.

(51) Int. Cl.
*A61L 24/06* (2006.01)
*C08F 220/18* (2006.01)
*C08F 222/22* (2006.01)

(52) U.S. Cl.
CPC ........ *A61L 24/06* (2013.01); *C08F 220/1818* (2020.02); *C08F 222/22* (2013.01); *C08F 2810/20* (2013.01)

(58) Field of Classification Search
None
See application file for complete search history.

(56) References Cited

U.S. PATENT DOCUMENTS 5,156,911 A * 10/1992 Stewart ...................... C09J 7/35 424/448
2015/0126834 A1 5/2015 Wang et al.

FOREIGN PATENT DOCUMENTS

JP 2000271204 A 10/2000

OTHER PUBLICATIONS

Extended European Search Report dated Nov. 21, 2024 for European Application No. 22746798.2.
De Crevoisier et al. “Switchable tackiness and wettability of a liquid crystalline polymer”. Science. Aug. 20, 1999;285(5431):1246-9.
Kamperman et al. “Switchable adhesion by chemical functionality and topography.” Journal of Materials Chemistry 22 (2012): 19390-19401.
PCT International Search Report and Written Opinion dated Jun. 2, 2022 for PCT Application No. PCT/US22/14549.

* cited by examiner

*Primary Examiner* — Sheeba Ahmed
(74) *Attorney, Agent, or Firm* — GATES & COOPER LLP

(57) ABSTRACT

A composition of matter useful as a bioadhesive including a bistable adhesive polymer. The bistable adhesive polymer includes one or more polymer backbones; side-chains attached to each of the polymer backbones; and one or more transition temperatures between a crystalline state and an amorphous state. The one or more transition temperatures are such that the polymer transitions from the crystalline state to the amorphous state upon physical contact with biological tissue having a temperature higher than the transition temperature. The polymer adheres or attaches to the biological tissue in the amorphous state and can be peeled from the biological tissue when cooled below the transition temperature to the crystalline state.

20 Claims, 37 Drawing Sheets f a c b d e

REVERSIBLE BIOADHESIVE

CROSS REFERENCE TO RELATED APPLICATIONS

This application claims the benefit under 35 U.S.C. Section 119(e) of co-pending and commonly-assigned U.S. Provisional Patent Application No. 63/143,163, filed Jan. 29, 2021, by Qibing Pei, Meng Gao, Hanxiang Wu, and Zhixin Xie, entitled "A REVERSIBLE BIOADHESIVE," which application is incorporated by reference herein.

STATEMENT REGARDING FEDERALLY SPONSORED RESEARCH AND DEVELOPMENT

This invention was made with government support under Grant Number 1638163, awarded by the National Science Foundation. The government has certain rights in the invention.

BACKGROUND OF THE INVENTION

1. Field of the Invention

The present disclosure relates to adhesives and methods of making the same.

2. Description of the Related Art (Note: This application references a number of different publications or references as indicated throughout the specification by one or more reference numbers in superscript brackets [x]. A list of these different publications or references ordered according to these reference numbers can be found below in the section entitled "References." Each of these publications or references is incorporated by reference herein.)

Skin-attachable electronic devices with conformal and biocompatible adhesion to skin surfaces, often referred to as electronic skins (E-skins),[1-2] are desired for compact and convenient human-machine interfaces (HMI) and can obtain accurate and reliable biological/physical information. [4-7] To date, various critical E-skin components and systems have been developed. Among them, triboelectric nanogenerators (TENGs) have shown promise as an in-situ energy source for E-skins, as well as a means to detect and monitor human physical activities.[8-11] TENGs can directly convert mechanical energy into electricity based on the coupling effect of contact electrification and electrostatic induction, with the advantage of structural simplicity, diverse material options, and high conversion efficiency.[12,13] Hence, the utilization of E-skins with autonomous powering ability and active sensing capacity is of great significance for the realization of a self-powered mechanosensation HMI system.

Another important and fairly unique element of the E-skins is its ability to be directly adhered to the skin, with strong yet reversible bonding. Conventional adhesive patches studied for E-skins mainly include bioinspired microstructured adhesives, pressure sensitive adhesives, and chemical adhesives. The bioinspired microstructured adhesives, such as gecko foot-inspired micropillar arrays[14] or suction cup architectures inspired by octopus suckers[15], demonstrate strong adhesion on smooth surfaces, while their adhesion on uneven and soft surfaces is poor. Thus they may not be a good option for skin which is uneven, soft, and often hairy. Pressure sensitive adhesives[16] which bind to surfaces upon contact and light pressure, tend to have inadequate adhesion leading to premature detachment. Chemical adhesives, which form complementary functional groups such as carbon-carbon, [17] amide, [18] siloxane, [19] and carbon-nitrogen[20] with adherend, can offer strong and secure adhesion for E-skins, but could be difficult to remove after use. Additionally, the removal process may trigger inflammatory responses that lead to irritation and pain[21]. Since the covalent bonds are broken and cannot be reformed once the patch is removed, E-skins based on chemical adhesion are single use devices.

The ideal E-skins should be capable of repeated attachments and detachments, similar to a wrist watch, and as a result, reversible debonding-on-demand (DoD) adhesives have gained attention for wearables and skin-attachable E-skins. Chen et al. introduced a bio-adhesive hydrogel that can be detached by cleaving both physical amide bonds and covalent disulfide bonds using an aqueous solution containing sodium bicarbonate and glutathione.[22] This DoD adhesive demonstrates both tough adhesion and triggerable detachment. However, the detachment requires the specially formulated solution to trigger and the hydrogel adhesive cannot be reused without drying out the absorbed water. Other detachable adhesion materials have also been reported with noncovalent or dynamic covalent adhesion bonds that are cleaved in response to external stimuli such as UV light,[23,24] chemicals,[25,26] humidity,[27] magnetic fields, [28] and electrical current.[29] While these triggers could provide switchable adhesion properties with adequate on/off adhesive strength ratios, they require external stimuli that may be inaccessible or harsh for use on human skin, and limited to particular types of substrate.

SUMMARY OF THE INVENTION

In the field of skin-attachable electronics, debonding-on-demand (DoD) adhesives triggered by mild, efficient, and accessible stimuli can facilitate repeated usage with negligible damage to skin. The present disclosure reports on compositions of matter useful as an adhesive. As described in one or more examples herein, a versatile method has been developed to fabricate biocompatible bonding/debonding bistable adhesive polymers (BAPs) with skin temperature triggered conformal adhesion and room temperature triggered easy detaching.

An illustrative example application of the BAP in a mechanosensitive communication system is demonstrated. The BAPs in this example are designed by incorporating stearyl acrylate (SA) and tetradecyl acrylate (TA) into a chemically cross-linked elastomer, where a semicrystalline melting transition between 26° C. and 32° C. results in high adhesive flowability and large energy dissipation. An optically transparent and mechanically compliant debonding-on-demand triboelectric nanogenerator (DoD-TENG) is fabricated using the BAP as the DoD substrate, a polydimethylsiloxane (PDMS) elastomer as the electrification layer, and an ion-conductive elastomer as the electrode. Furthermore, the DoD-TENG can serve as a human-machine interface for a self-powered drone navigation system.

However, the present invention can be embodied in many ways including, but not limited to, the following examples.

1. A composition of matter useful as an adhesive, comprising:

a bistable adhesive polymer comprising:

one or more polymer backbones;

side-chains attached to each of the polymer backbones;

one or more transition temperatures between a crystalline state and an amorphous state, wherein:

the one or more transition temperatures are such that the polymer transitions from the crystalline state to the amorphous state upon physical contact with a substrate having a temperature higher than the transition temperature; and the polymer adheres or attaches to the substrate in the amorphous state and can be peeled from the substrate when cooled below the transition temperature to the crystalline state.

2. A bioadhesive comprising the composition of matter of example 1, wherein: the side-chains comprise linear alkyl chains, the chains are:

crystalline at a temperature below a temperature of skin or living tissue ("skin or living tissue temperature"), and amorphous at the skin or living tissue temperature of the substrate comprising skin or the living tissue on which bioadhesive is applied;

the bioadhesive has a first storage modulus less than 2 MPa at the skin or living tissue temperature;

the bioadhesive, comprising the polymer in the amorphous state, adheres with the skin or living tissue;

the bioadhesive has a second storage modulus, at some temperature below the skin or living tissue temperature, that is at least 10 times greater than the first storage modulus at the skin or living tissue temperature;

the bioadhesive is removable from the skin or living tissue by cooling to below the skin or living tissue temperature; and after removal from the skin or living tissue, the bioadhesive adheres to the skin or living when it is placed again on the skin or living tissue.

3. An adhesive assembly comprising the bioadhesive or adhesive of examples 1 or 2.

4. The bioadhesive of example 1 or 2, wherein the bioadhesive:

has the first storage modulus less than 1 MPa at the skin or living tissue temperature; and has the second storage modulus at the temperature below the skin or living tissue temperature that is at least 10 times greater than the first storage modulus at skin or living tissue temperature.

5. The bioadhesive or composition of matter of any of the examples 1-4, wherein:

said skin or living tissue temperature is greater than 30° C., but less than 45° C.; and said some temperature below skin or living tissue temperature is less than 26° C.

6. The bioadhesive or composition of matter of any of the examples 1-5, wherein the polymer comprises polymer chains that are crosslinked to form an elastomer network.

7. The bioadhesive or composition of matter of any of the examples 1-6, where the polymer chains are formed from a liquid formula comprising at least an acrylate monomer or a methacrylate monomer, an oligomer comprising an acrylate oligomer or a methacrylate oligomer, and a polymerization initiator.

8. The bioadhesive or composition of matter of example 7, wherein the acrylate oligomer comprises at least one oligomer selected from CN9004, CN9021, CN966J75, CN964, urethane diacylate, polyethylene glycol diacrylate, polypropylene glycol diacrylate, hexane diol diacrylate, trimethylolpropane triacrylate, urethane dimethacylate, polyethylene glycol dimethacrylate, polypropylene glycol dimethacrylate, hexanediol dimethacrylate, trimethylolpropane trimethacrylate, or a mixture thereof.

9. The bioadhesive or composition of matter of any of the examples 1-8, wherein the appendant linear alkyl chains comprise at least one compound selected from octadecyl, hexadecyl, tetradecyl, dodecyl, or mixtures thereof.

10. The bioadhesive or composition of matter of any of the examples 1-9, wherein the acrylate monomer or the methacrylate monomer comprises at least one monomer selected from octadecyl acrylate, hexadecyl acrylate, tetradecyl acrylate, dodecyl acrylate, octadecyl methacrylate, hexadecyl methacrylate, tetradecyl methacrylate, dodecyl methacrylate, or a mixture thereof.

11. The bioadhesive or composition of matter of any of the examples 7-10, wherein the polymerization initiator is a photoinitiator or thermal initiator which may initialize a free radical polymerization of a vinyl compound.

12. The bioadhesive or composition of matter of any of the examples 7-11, wherein the monomer and the oligomer are mixed at a weight ratio in the range of 1:2 to 4:1.

13. The bioadhesive or composition of matter of any of the examples 7-12, wherein the acrylate monomer or the methacrylate monomer comprises octadecyl acrylate and tetradecyl acrylate mixed at the weight ratio in the range of 1:3 to 4:1.

14. The bioadhesive or composition of matter of any of the examples 7-13, fabricated by a process comprising:

mixing the monomer, oligomer, and polymerization initiator to form a uniform solution;

casting, printing, or spin-coating the uniform solution to form a solution layer of the uniform solution; and exposing the solution layer to ultraviolet light or heat to cure the solution layer.

15. The bioadhesive or composition of matter of any of the examples 1-14, coated as a layer in an adhesive assembly, wherein the layer has a thickness in the range of 1-1000 micrometers.

16. An adhesive assembly comprising the composition of matter of any of the examples 1-15, wherein the adhesive assembly is a biosensor placed on the substrate comprising a neural interface, living tissue, or skin 17. The adhesive assembly comprising the composition of matter of any of the examples 1-16, wherein the biosensor a multi-electrode array, a nerve cuff electrode, a cortical recording or stimulating electrode, a spinal cord recording or stimulating electrode, a peripheral recording or stimulating electrode, an epidermal electrode, or an epidermal sensor.

18. A prosthetic or plastic surgical implant comprising the bioadhesive of any of the Examples 2-15, wherein the prosthetic or plastic surgical implant substitutes or augments a limb, a hand, a foot, a finger, a toe, a breast, an ear, or a nose.

19. An anatomical model comprising the bioadhesive of any of the examples 2-15, wherein the anatomical model is used to create a tissue phantom, a surgical suture anchor, a stent, a valve, a catheter, or a synthetic tendon.

20. The bioadhesive or any of the examples 2-19, comprising a reversible dry adhesive.

21. The composition of matter of example 1, wherein:

the polymer comprises a copolymer including a combination or mixture of a first component, a second component, a third component, wherein:

the first component has a first transition temperature below the temperature of the biological tissue, the second component has a second transition temperature greater than the temperature of the biological tissue, the third component has a storage modulus tailoring a polymer storage modulus of the copolymer such that the storage modulus of the third component and the polymer storage modulus are below 2 MPa at the temperature of the biological tissue, and the first transition temperature and the second transition temperature are such that the copolymer has the one or more transition temperatures above the first transition temperature but below the temperature of biological tissue.

22. The composition of matter of example 21, wherein the copolymer includes at least a fourth component having a fourth transition temperature between the first transition temperature and the second transition temperature.

23. The composition of matter of example 21, wherein the first component and the second component form crystalline aggregates in the crystalline state and act as a matrix plasticizer for the side-chains in the amorphous state, the polymer has lower viscosity so as to flow, conform, and stick to a surface the substrate comprising biological tissue in the amorphous state in response to an external force, and the polymer has higher elasticity and higher viscosity in the crystalline state, as compared to in the amorphous state, reducing the adhesion to the biological tissue and distributing a stretching force over the polymer mitigating against rupturing when the polymer is peeled from the biological tissue.

24. The composition of matter of any of the examples 1 or 21-23, wherein:

the adhesive comprises a film comprising the polymer, and the film has a smoother surface interfacing with substrate comprising the biological tissue in the crystalline state and a rougher surface interfacing with the biological tissue in the amorphous state.

25. The composition of matter of any of the examples 1 or 21-24, wherein the side chains comprise linear alkyl chains.

26. The composition of matter of any of the examples 21-25, wherein the first component, the second component, and the third component each comprise an acrylate or methacrylate.

27. The composition of matter of any of the examples 21-26, wherein:

the first component and the second component each independently comprise at least one of stearyl acrylate, octadecyl acrylate, hexadecyl acrylate, tetradecyl acrylate, dodecyl acrylate, octadecyl methacrylate, hexadecyl methacrylate, tetradecyl methacrylate, dodecyl methacrylate, or a mixture thereof, and the third component comprises at least one of CN9004, CN9021, CN966J75, CN964, urethane diacylate, polyethylene glycol diacrylate, polypropylene glycol diacrylate, hexane diol diacrylate, trimethylolpropane triacrylate, urethane dimethacylate, polyethylene glycol dimethacrylate, polypropylene glycol dimethacrylate, hexanediol dimethacrylate, trimethylolpropane trimethacrylate, or a mixture thereof.

28. The composition of matter of any of the examples 21-27, wherein:

a first weight ratio of the first component to the second component is such that the copolymer has the transition temperature below 32 degrees Celsius, and a second weight ratio of the third component to a combination of the first component and the second component is such that the polymer's storage modulus (G') reduces by a factor of at least 1000 in the amorphous state as compared to the crystalline state.

29. The composition of matter of any of the examples 21-28, wherein the first weight ratio W1 is $1:2 \le W1 \le 4:1$ and the second weight ratio W2 is $1:3 \le W2 \le 4:1$.

30. The composition of matter of any of the examples 21-29, wherein the side-chains comprise at least one linear alkyl chain, the at least one linear alkyl chain comprising at least one of an octadecyl, a hexadecyl, a tetradecyl, a dodecyl, or a mixture thereof.

31. The method or composition of matter of any of the examples 1 or 21-30, wherein the polymer comprises the structure:

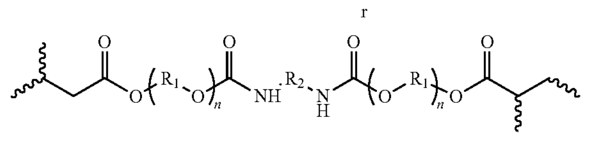

32. The composition of matter of any of the examples 1 or 21-31, wherein the first component is stearyl acrylate, the second component is tetradecyl acrylate, and the third component is urethane diacrylate, and the copolymer optionally includes a fourth component hexadecyl acrylate.

33. The composition of matter of any of the examples 1 or 21-32, wherein the polymer comprises an adhesive that is reversibly bistable, the adhesive adhering to substrate comprising the biological tissue after at least 10 cycles, each cycle comprising adhering and peeling the polymer from the biological tissue.

34. The composition of matter of any of the examples 1 or 21-33, wherein the substrate comprises biological tissue comprising skin tissue or bone tissue.

35. A device comprising an adhesive including the composition of matter of any of the examples 1-34.

36. The device of example 35, wherein the device comprises an electronic skin (E-skin), a human machine interface, an electrode, a prosthetic, a surgical implant, a tissue phantom, a surgical suture anchor, a stent, a valve, a catheter, or a synthetic tendon, a biosensor, or an anatomical model.

37. The device of example 35, wherein the device comprises a human machine interface wherein the copolymer reversibly attaches the human machine interface to a body part and touching the human machine interface modulates transmission of an analog or digital signal controlling a machine.

38. The device of example 37, wherein the machine comprises a drone and the touching controls a motion of the drone.

39. The device of example 37 or 38, wherein the body part comprises one or more fingers or a hand.

40. A method of making a composition of matter useful as a bioadhesive, comprising:

polymerizing a combination of a first component, a second component, and a third component to form a copolymer, wherein:

the first component has a first transition temperature below the temperature of the biological tissue, the second component has a second transition temperature greater than the temperature of the biological tissue, the third component has a storage modulus tailoring a polymer storage modulus of the copolymer such that the storage modulus of the third component and the polymer storage modulus are below 2 MPa at the temperature of the biological tissue, and the first transition temperature and the second transition temperature are such that the copolymer has the one or more transition temperatures above the first transition temperature but below the temperature of biological tissue.

41. The method of example 40, wherein the polymerizing includes:

mixing the first component, the second component, and the third component with a polymerization initiator in a solution; and curing the solution to form the copolymer.

42. The method or composition of matter of any of the examples 1 or 21-41, wherein the first component, the second component, and the third component are crosslinked.

43. The method of any of the examples 39-41 used to make the composition of matter of any of the examples 1 or 21-39.

44. The method or composition of matter of any of the examples 1-43, wherein the adhesion of the polymer in the amorphous state is increased by a factor of at least 5 as compared to in the crystalline state, as measured by a 90 degree peeling test.

45. The method or composition of matter of example 44, wherein:

the peeling strength of the polymer from the substrate comprising artificial skin is at least 50 N/m in the amorphous state, as measured in a 90 degree peeling test, and the peeling strength of the polymer from the artificial skin is less than 10 N/m in the crystalline state, as measured in the 90 degree peeling test.

BRIEF DESCRIPTION OF THE DRAWINGS

Referring now to the drawings in which like reference numbers represent corresponding parts throughout.

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Technical Description

Embodiments of the present invention include a new reversible DoD biocompatible skin adhesive that utilizes the temperature difference between the human body and its surrounding environment. This bistable adhesive polymer (BAP) is relatively stiff and not adherent at ambient temperature but soft and sticky at elevated temperatures.

Example BAP

The BAP is a copolymer comprising stearyl acrylate (SA) and tetradecyl acrylate (TA) in a chemically cross-linked elastomer network. The crystalline melting transition of the mixed stearyl and tetradecyl chains between 26° C. and 32° C. leads to a large modulus reduction and high flowability. BAP films are sticky above 32° C., allowing E-skins to adhere to skin and stay attached during routine activities. It becomes non-tacky and easily removable from the skin at temperatures below 26° C. which are easily obtainable using tap water.

To demonstrate the potential of BAPs for E-skin applications, a debonding-on-demand TENG (DoD-TENG) was fabricated using the BAP as the DoD substrate. The TENG function was generated using a dielectric elastomer as the electrification layer and an ionic hydrogel as the electrode. The DoD-TENG device is optically transparent and mechanically compliant during the on-skin usage, and becomes opaque and relatively stiff when freestanding in the air. The capabilities of this DoD-TENG were demonstrated through a human-machine interface for self-powered sensor networks and mechanosensitive communication systems.

Figure 1:
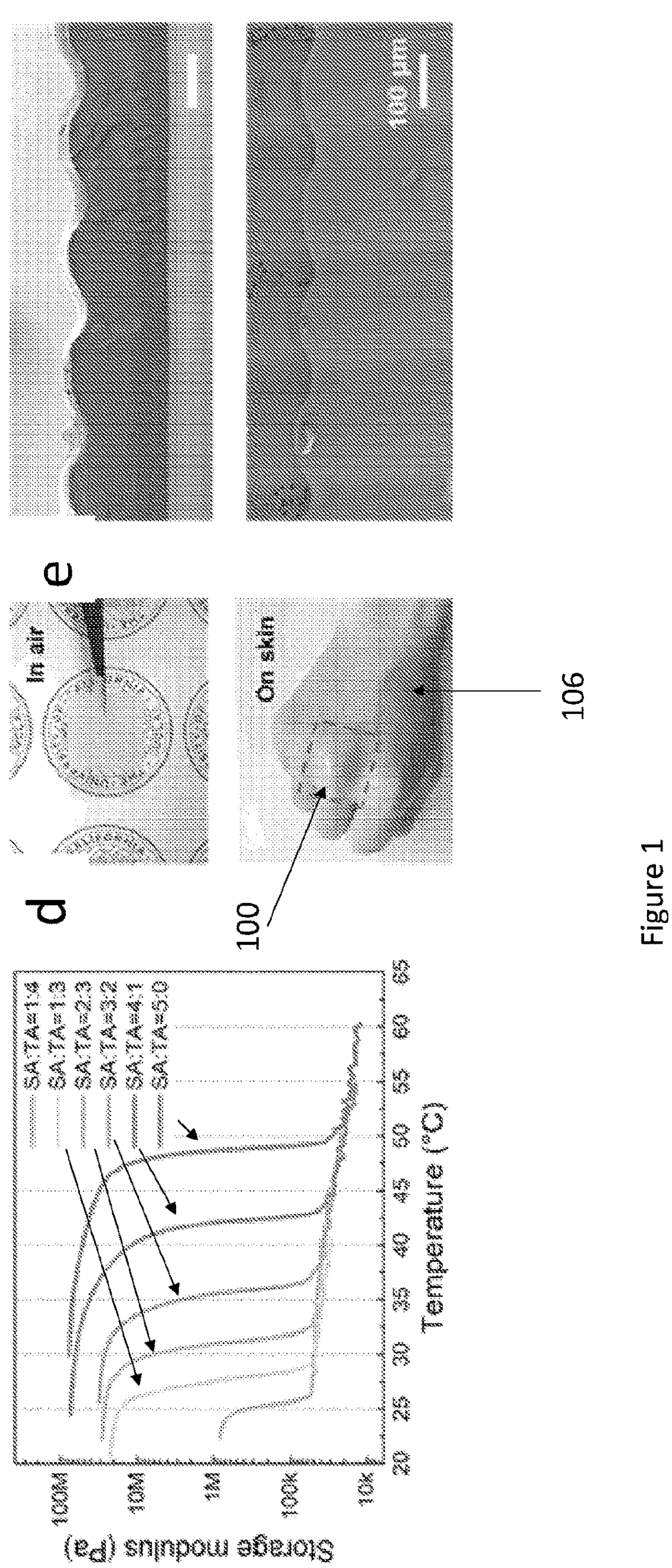
FIG. 1. *a*) Molecular structures of BAP precursors and the polymerized BAP.
Figure 1A:
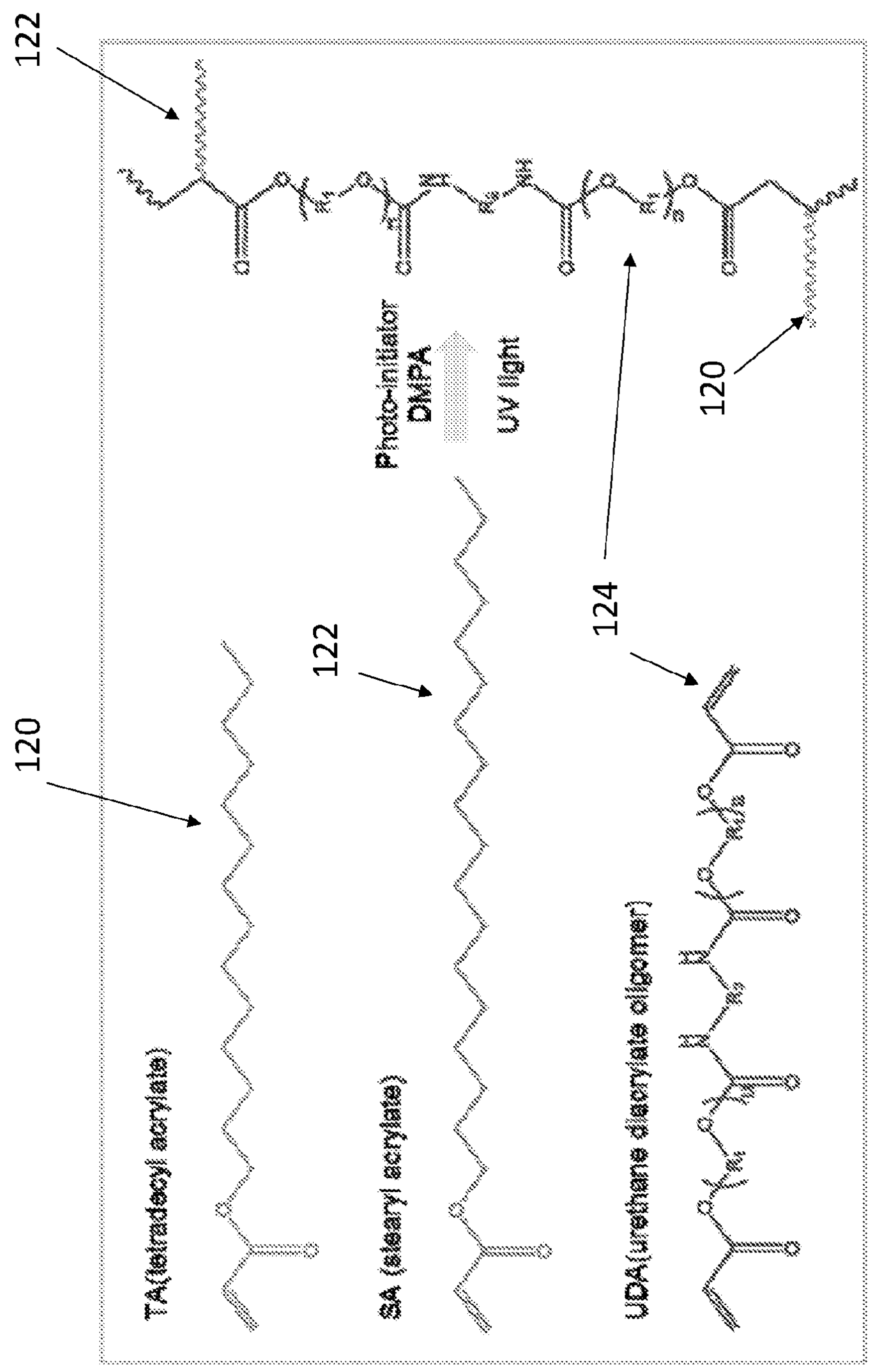
FIGS. 1*b*)-1*h*). Bonding/debonding mechanism of BAP films. *b*) Schematic illustration of BAP's crystalline-to-molten phase transition of the linear alkyl chains(i) and the interfacial behavior during peeling (ii). *c*) Temperature-modulus curves of BAPs with difference SA/TA ratios. *d*) Photographs of a BAP patch held in the air (upper) and attached to a hand (lower). *e*) Scanning Electron Microscope (SEM) images taken at 90° and 45° angles of a BAP film placed on a microgrooved surface and formed conformal structure at heated temperature (40° C.)*f*} 90° and 45° *g*) SEM images of BAP film placed on laser-cutted PET microgroove pattern both at room temperature (21° C.). *h*) Photographs of the BAP patch strongly attached to the forearm when subject to external forces such as tension, compression, and torsion. For a more vivid illustration, Rhodamine 19 is used to stain on the BAP patch attached onto the forearm.

The BAP polymer was synthesized by copolymerizing a mixture of stearyl acrylate (SA), tetradecyl acrylate (TA) and a long chain urethane diacrylate (UDA, CN9021) oligomer via photo-polymerization. The molecular structures of these key ingredients are shown in FIG. 1*a*. SA was selected in the copolymer system as it exhibits a narrow melting temperature range ($T_m$) between 47° C. and 50° C.[30] TA was added to lower the phase change temperature below the temperature range of human skin. UDA was chosen to form the elastomeric network as the homopolymer of UDA has a modestly low modulus (0.827 MPa) at room temperature and a large elongation at breakage of 1100%.[30] The BAP films were fabricated by casting the monomer mixture into a thin liquid layer and were subsequently cured under UV exposure to form solid-state films.

Figure 1B:
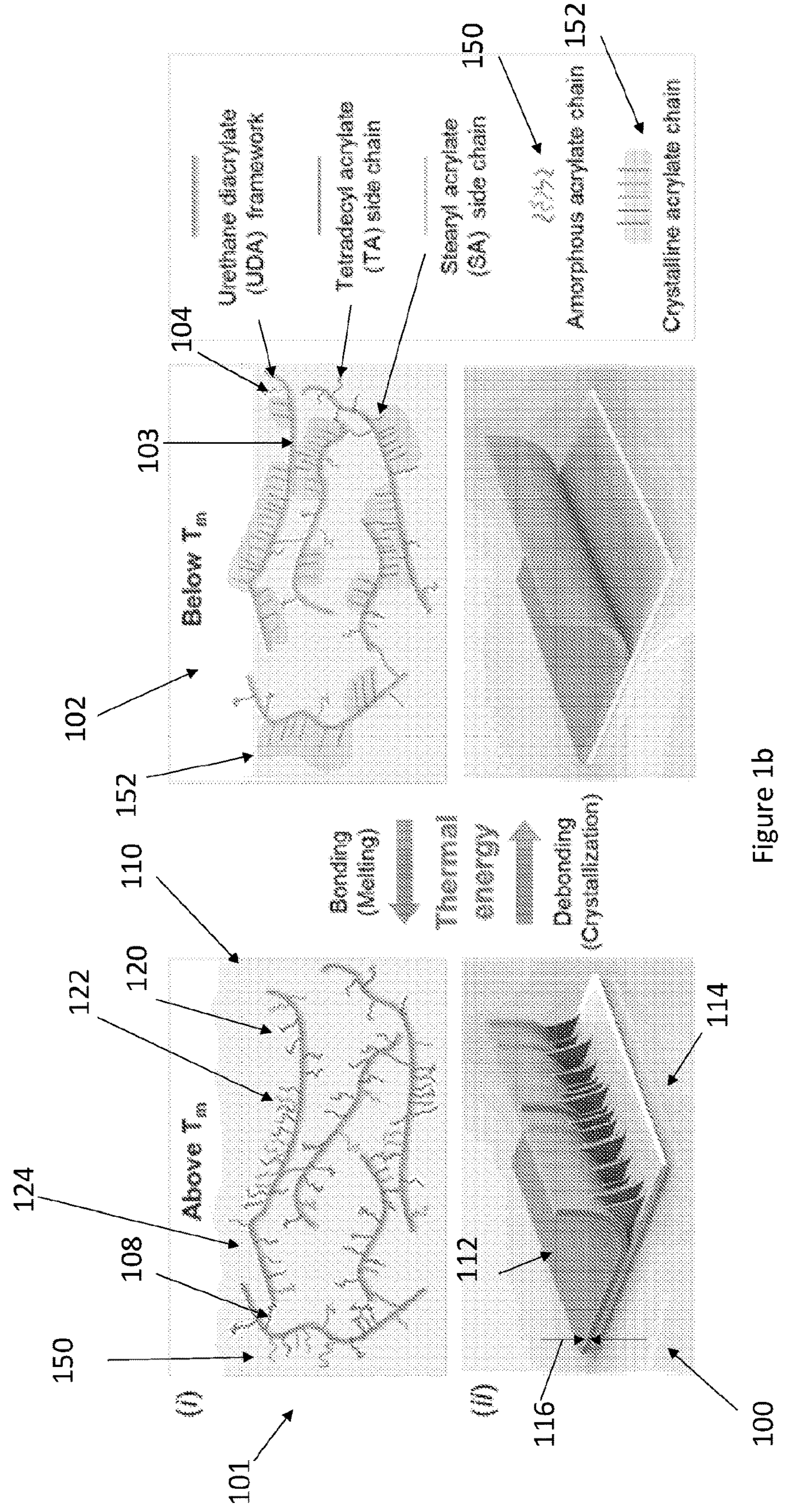

The bonding/debonding mechanism of the BAP is shown in FIG. 1*b*. The adjustable adhesive behavior is ascribed to the skin-temperature triggered rigid-to-rubbery (semicrystalline-to-amorphous) transition (FIG. 1*bi*). In the SA/TA-UDA copolymer-based BAP, the crystalline aggregates of SA and TA moiety act as hard segments in the copolymers and lead to a rigid phase when $T<T_m$. As the crystalline long alkyl side-chains melt at elevated temperatures, the rigid polymer becomes soft rubbery, with the molten stearyl and tetradecyl chains acting as the matrix plasticizer. Unlike the semicrystalline state, the molten state ensures high flowability, and the film can readily flow and conform to the target surface. Meanwhile, the polymer's low modulus and low viscosity enabled by its soft alkyl chains give the film a high energy dissipation property.[31] During peeling and deformation, the stretching force is distributed over a large body of the film, thus mitigating the tendency of cleaving the adhesion front or rupturing the local structure.[32] Therefore, the BAP exhibits physical adhesive characteristics above $T_m$ and shows a thread-like microstructure at the peeling interface (FIG. 1*bii*).

The transition temperature of the BAP was tuned by modifying the SA:TA weight ratio and measured via dynamic mechanical analysis (DMA). The test was conducted at a temperature ramping rate of 3° C./min across the phase transition temperature range and a mechanical loading frequency of 1 Hz. As illustrated in FIG. 1*c*, the rigid-to-rubbery transition temperature decreases with an increase of TA due to its shorter alkyl chain compared to SA. At a SA:TA weight ratio of 2:3, the BAP has a narrow transition temperature range between 26-32° C. which is just below the surface temperature of skin, making it an ideal candidate for a skin-temperature triggered bistable polymer. The film possesses a steep stiffness change of ~1000 times from a storage modulus (G') of about 30.8 MPa to 0.03 MPa. Once the transition is completed, the storage modulus does not change significantly with further temperatures increase.

Figure 1F:
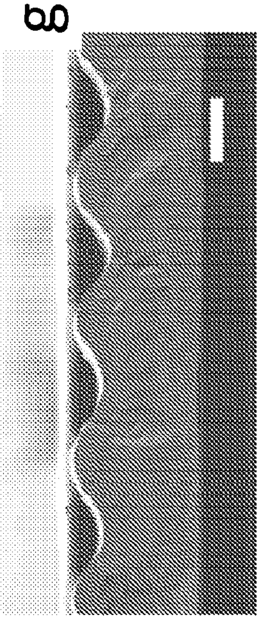
Figure 1G:
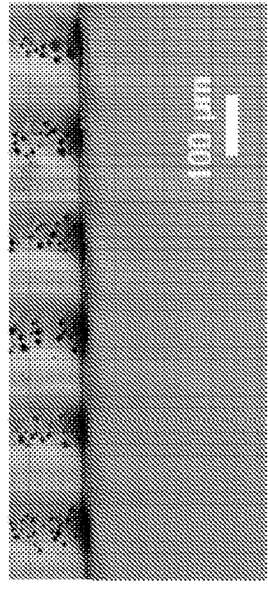
Figure 1H:
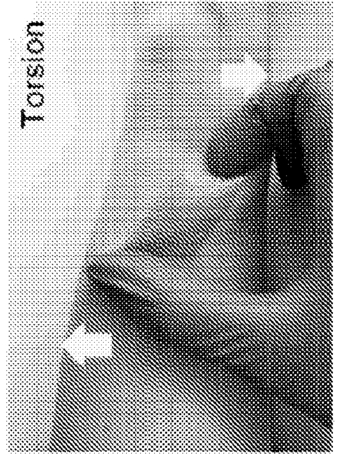
Figure 1H:
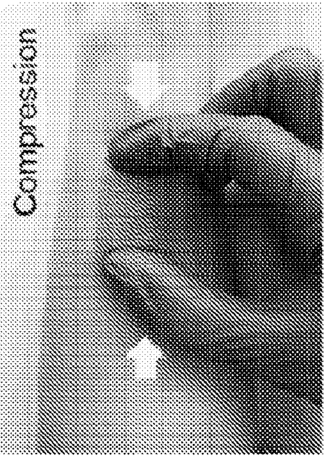
Figure 1H:
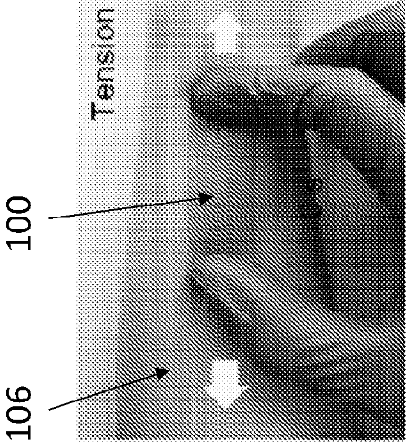

The unique phase transition property of the BAP allows it to be handled as a freestanding film at room temperature, but conform to human skin along the highly curved contours of knuckles at skin temperature (FIG. 1*d*). The patch could retain its position without delamination or tear despite the application of various external forces such as tension, compression, and torsion (FIG. 1*h*). The changes in the adhesion property and flowability of BAP under different temperatures are imaged by cross-sectional scanning electron microscope (SEM) at 45° and 90° angles (FIG. 1*e*-1*g*). BAP films are placed on a laser-cut PET micro-groove pattern substrate under the ambient environment (21° C.), and heated temperature (40° C.), respectively. At room temperature, the BAP film maintains its original planar shape. At 40° C., it conforms smoothly and tightly along the microstructured grooves.

In order to quantitatively assess the bonding strength of the BAP film, a standard 90° peeling test was conducted with a peeling rate of 50 mm/min. The schematic illustration of the test is presented in FIG. 2*a*. In a typical experiment, the bottom surface of the testing substrate is fixed onto the glass slide, while the BAP film is adhered to a thin stiff backing (polyimide, with a thickness of 90 μm), which prevents film elongation along the peeling direction. For BAP measured at 32° C., a typical adhesive thread-like microstructure is observed at the interface as the peeling propagates (FIG. 2*b*). When the film is cooled down to 21° C., the interface between BAP film and substrate is clear, which demonstrates poor adhesion performance as depicted in FIG. 2*c*, and the interface easily propagates along the BAP film without kinking or deformation.

Figure 2:
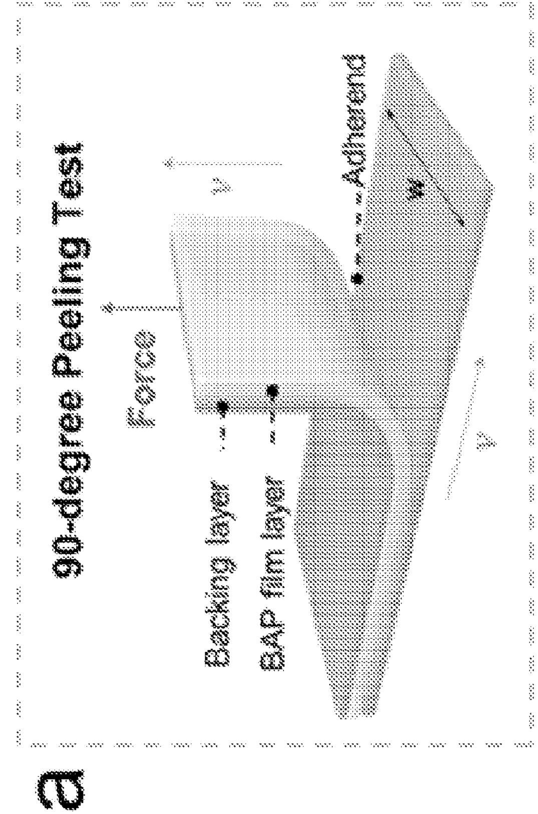
FIG. 2. Bonding/debonding performance of the BAP films. *a*) Scheme of 90° peeling test. *b-c*) Photographs of a BAP film being peeled off from an adherend at 32° C. and at 20° C. after being cooled with tap water. A yellow Kapton film is used as the stiff backing for the BAP film. *d*) Representative force-displacement curves of the peeling strength of a BAP film from an artificial skin system under 3 circumstances including heated to 32° C., cooled down to 21° C. in air and cooled down to 20° C. in water, respectively. *e*) Measured peel strengths of BAP attached to diverse adherends. *f*) Measured peel strengths of the BAP-artificial skin system under periodical temperature change from 32° C. to 20° C., illustrating reusability of the BAP film. *g*) schematic figure showing the peeling process of non-adhesive state and *h*) schematic figure showing the peeling process of the adhesive state. *i*) Representative fluorescent staining images of live (blue) and dead (red) assay of NIH3T3 cells after cultured with (*a*) and without (*b*) BAP film. Blue dots are nuclei of all live or dead cells stained by Hoechst33342, and red dots are nuclei of dead cells stained by Ethidium Homodimer III.
Figure 2:
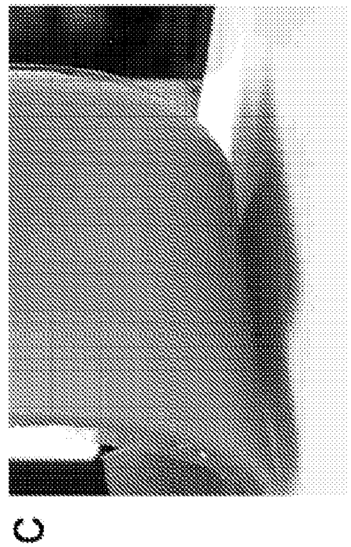
Figure 2:
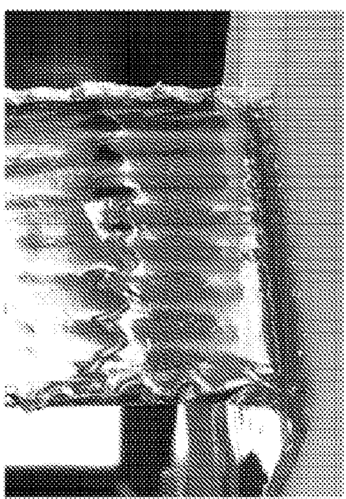
Figure 2:
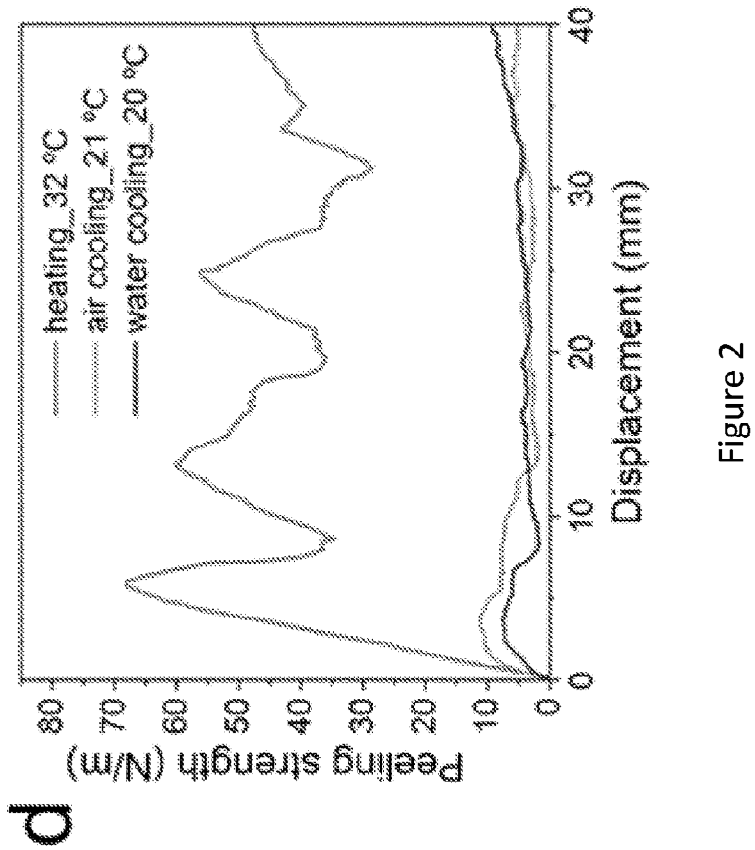
Figure 2:
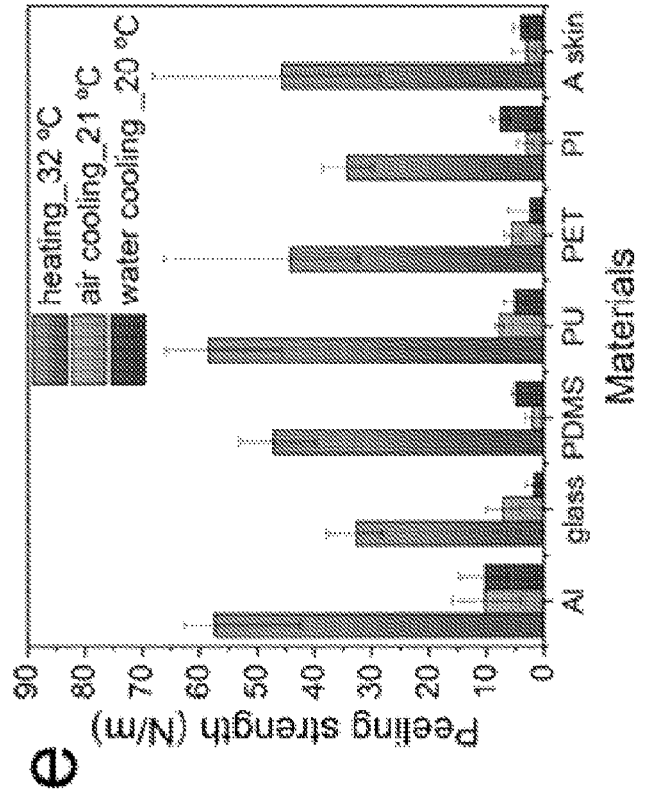
Figure 2:
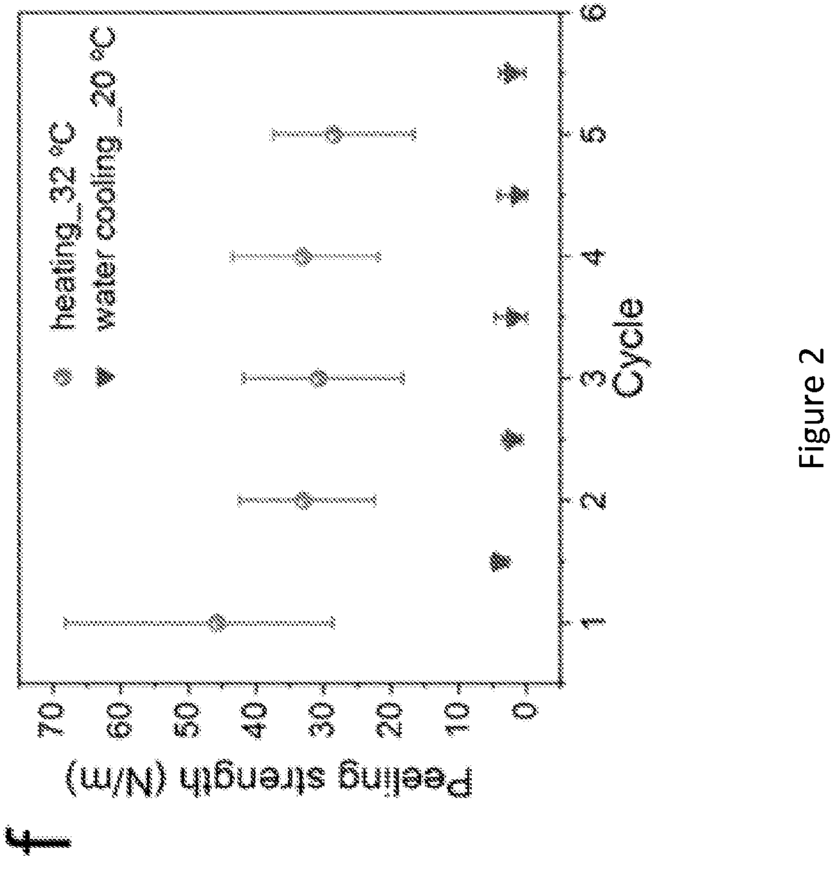
Figures 2G, 2H:
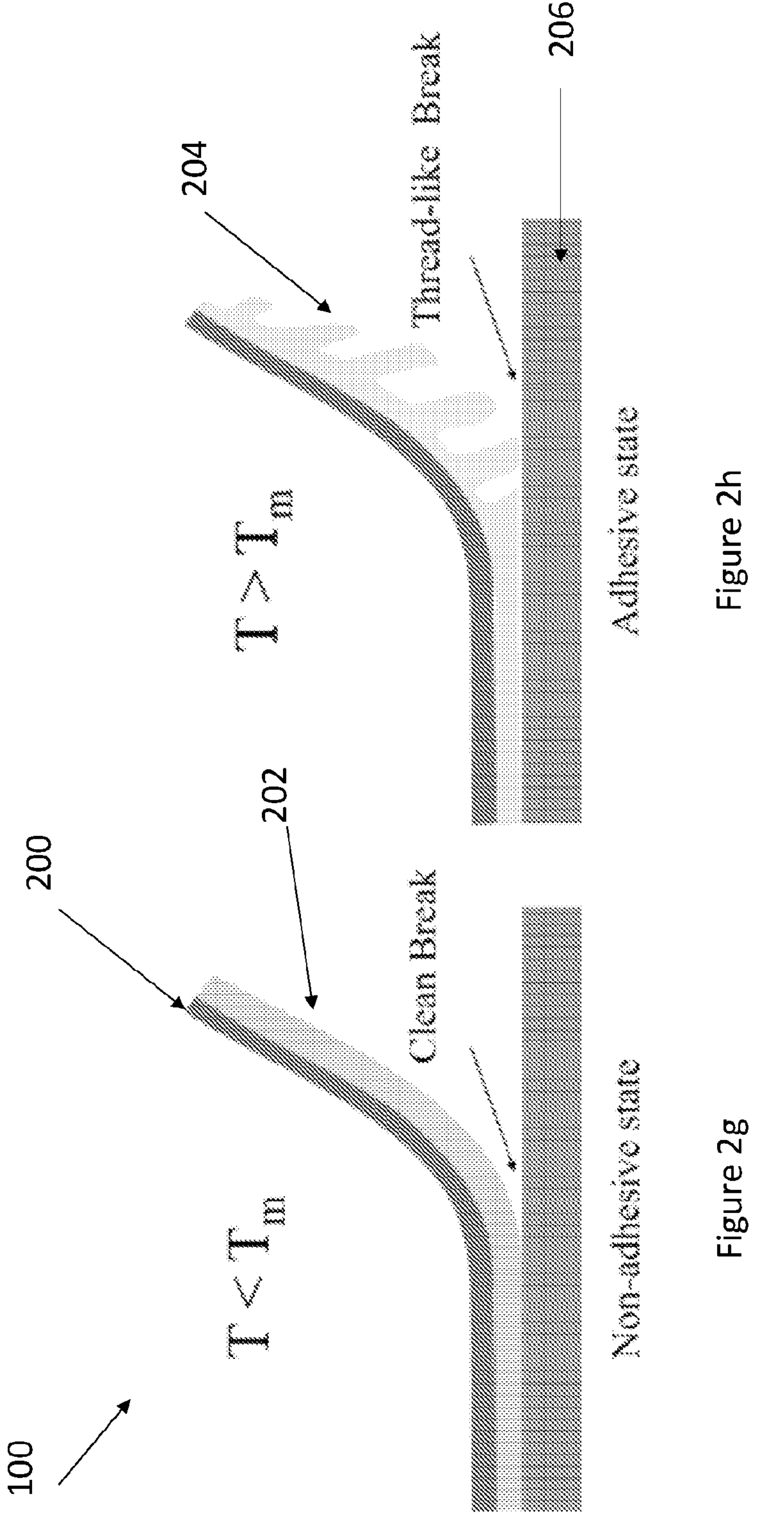

The measured bonding strengths are shown in FIG. 2*d*. At 32° C., the peel strength between BAP film and an artificial skin is 45.7 N/m, which drops to 3.0 N/m and 4.1 N/m when cooled down to room temperature with ambient air and water, respectively. The peeling curves at the heated state fluctuate somewhat periodically as the BAP needs to absorb sufficient energy along the peeling direction before the detachment with adherend takes place discretely (FIG. 2*g*). For a variety of other substrates (FIG. 2*e*), the average peel strengths are similarly high (32.7-57.5 N/m). However, BAP films at room temperature bond poorly to the test surfaces regardless of the cooling method. Therefore, apart from application in skin-mounted devices, the BAP could also be utilized in other specific scenarios on a diverse set of substrates where adjustable adhesive force is required.

Figure 2I:
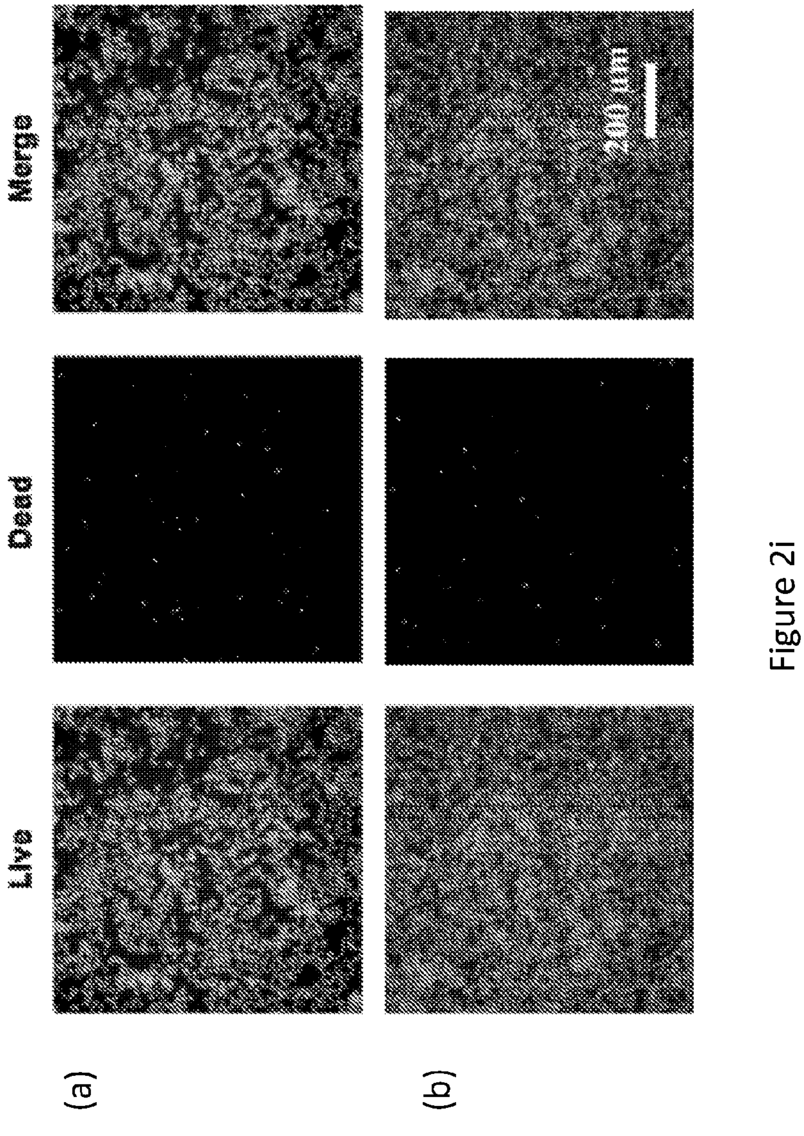

In order to examine the bonding/debonding stability of the BAP film for repeated uses, the peel strengths were measured at 20° C. and 32° C. for 6 cycles. It should be noted that the room temperature condition chosen here is provided by water cooling which is convenient to implement in the lab and also a practical approach for skin mounted electronics. As illustrated in FIG. 2*f*, the peel strength drops slightly at 32° C. after cycle 1 and then remains steady afterwards. At 20° C., peeling strength remains at low values. The BAP film is fairly stiff and easy to handle. As soon as the film makes contact with a human hand, it conforms to the epidermal structure. The film on the skin is difficult to peel off. When immersed in water for 1 min, it can be easily removed from the human hand, without leaving residue or causing skin discomfort. The peeled off film exhibits its stiff nature. After shaking off the surface water or air drying, it can be mounted on the skin again and strong adhesion is observed. Biocompatibility test of the BAP film was conducted, considering its conformal and intimate contact with human skin during usage. FIG. 2*i* shows fluorescent staining images of NIH3T3 cells' Live/Dead cell assay after cultured with (a) and without (b) BAP film for 1 day. The experimental samples and control samples show a negligible quantitative difference of live and dead cells, demonstrating a good cytocompatibility of the BAP film.

First Example Application: DOD-TENG

Figure 3:
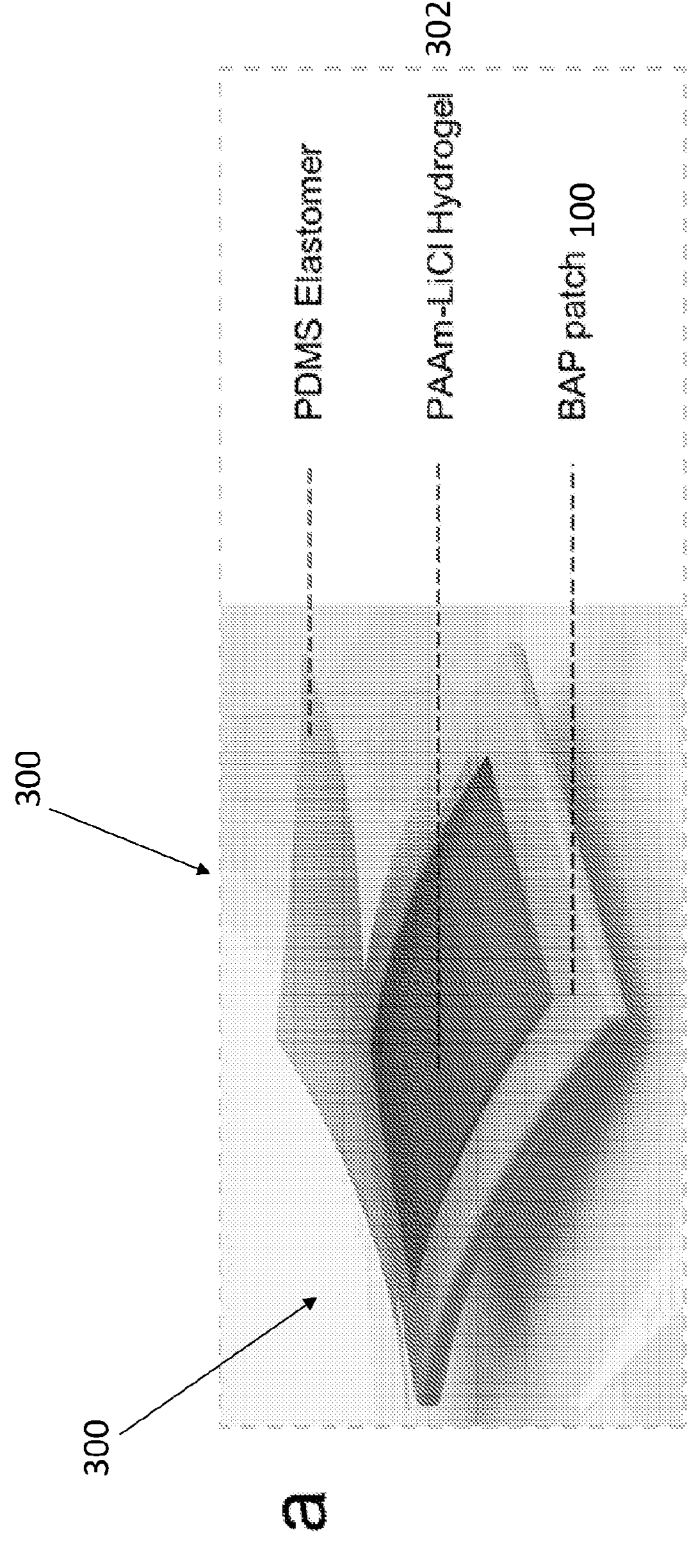
FIG. 3. Schematic design, manufacture, transparency, mechanical property, and electric output performance of the single-electrode DoD-TENG. *a*) Scheme of the DoD-TENG with sandwich structure. *b*) Schematic illustration of the fabricating process of the sandwich-structured DoDTENG. *c*) Working principle of the single electrode DoD-TENG with sandwich structure. *d*) Transmittance in the visible range of the BAP and the DoD-TENG tested at both room temperature (21° C.) and heated temperature (40° C.). *e*) Uniaxial tensile test of the PDMS elastomer, PAAm-LiCl hydrogel, and BAP measured at 32° C. *f*) Transmittance in the visible range of PDMS elastomer and PAAm-LiCl hydrogel tested at room temperature (21° C.). *g*) Uniaxial tensile test of the BAP measured at 21° C. and 32° C. *h-i*) Voltage and current output waveform of the DoD-TENG. *j*) The relation between power output and load resistance. *k*) Voltage profile of a 0.5 μF capacitor being charged by the DoD-TENG and used to power the thermistor. *l-m*) DoD-TENG working as power supply for commercial thermistor. *l*) Schematic of the power management circuit including a rectifying bridge by four diodes, and a capacitor for energy storage. *m*) Image of the testing layout with DoD-TENG attached to skin, connected to power management circuit and thermistor. *n*) Charging curves for different capacitors. *o*) The triboelectrification properties of various materials against the PDMS surface of the DoD-TENG. *p-r*) Triboelectric output of the DoD-TENG with different sets of tribo-positive materials, countering the tribo-negative PDMS layer on top of DoD-TENG.
Figure 3B:
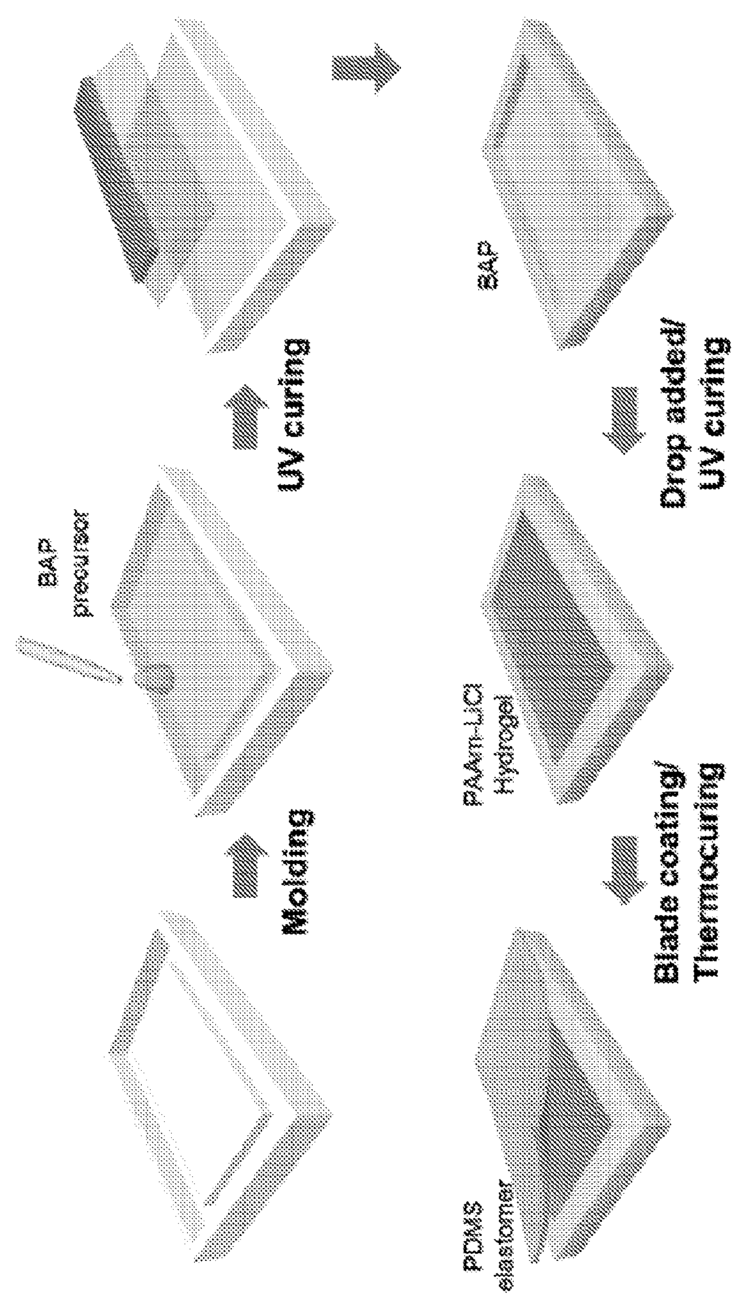
Figure 3C:
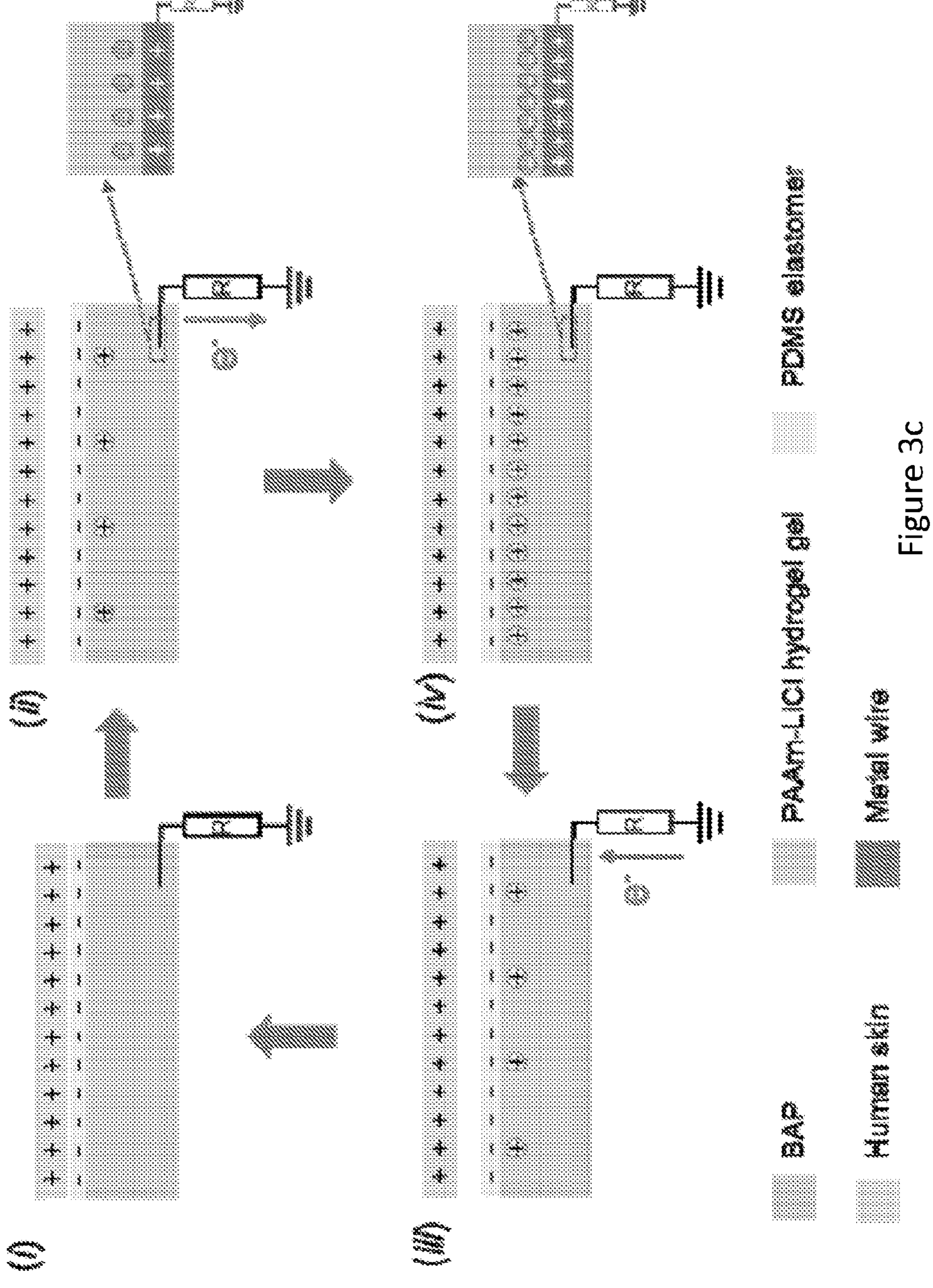
Figure 3:
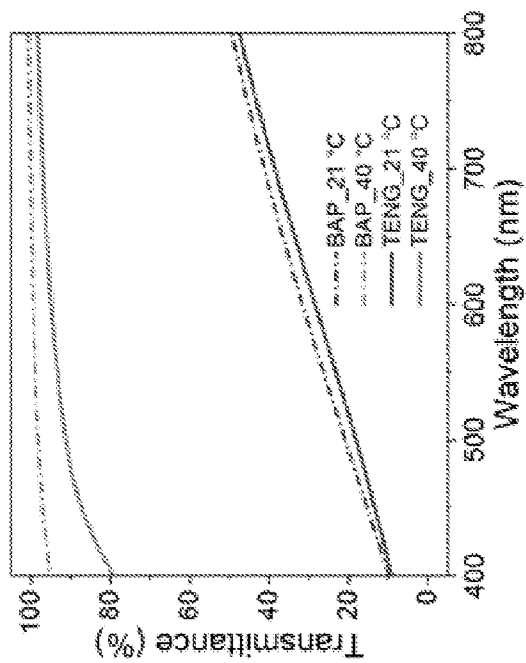
Figure 3:
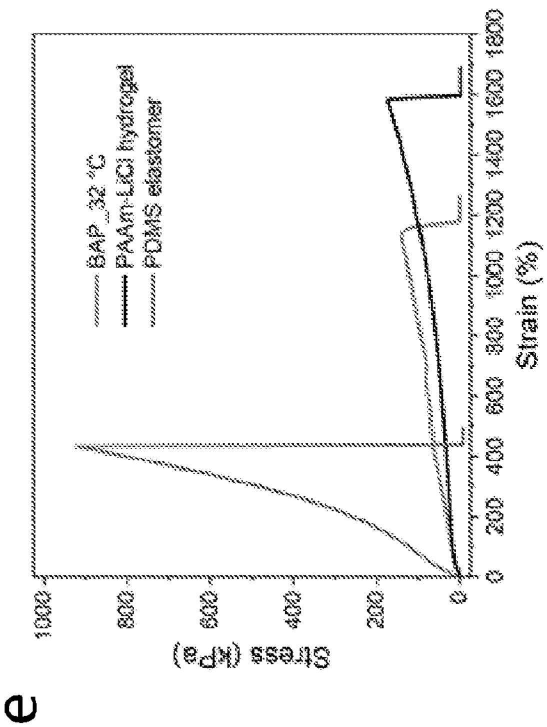

A single-electrode mode debonding-on-demand triboelectric nanogenerator (DoD-TENG) with a sandwich-like architecture was designed to demonstrate the potential of the BAP in E-skin devices, as shown in FIG. 3*a*. The DoD-TENG consists of a silicone rubber layer (polydimethylsiloxane, PDMS) acting as the tribo-negative material, a polyacrylamide (PAAm) hydrogel containing lithium chloride as the ionic current collector (PAAm-LiCl hydrogel), and the BAP as the DoD substrate. The fabrication process is described in the Experimental Section and FIG. 3*b*, and the working principle including contact triboelectrification and electrostatic induction is shown in FIG. 3*c*.

Figure 3F:
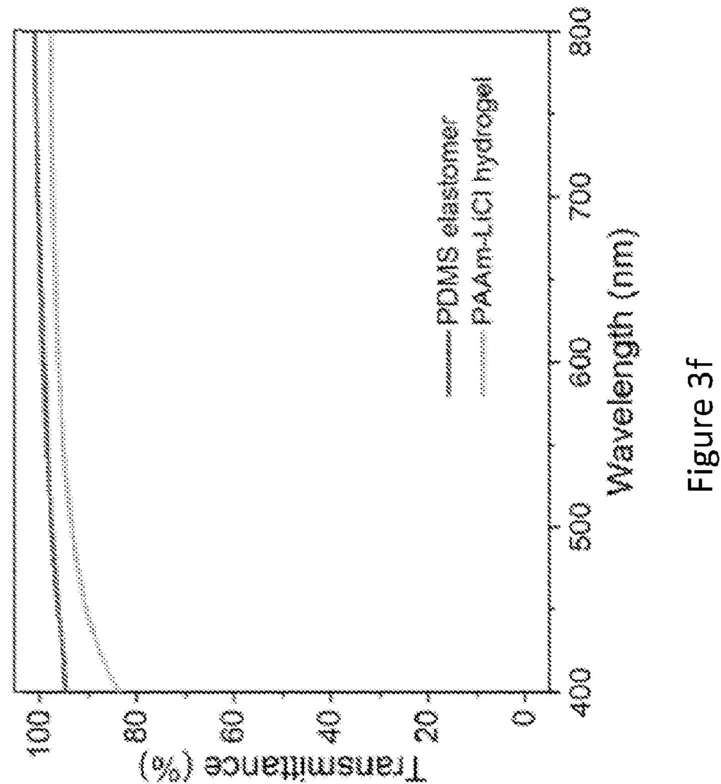

The transmittance of DoD-TENGs is measured and the results are shown in FIG. 3*d*. In the heated state (40° C.), the BAP shows an average transmittance of 99.1% in the visible spectrum (400-800 nm), and the corresponding DoD-TENG shows a transmittance of 93.4%. In contrast, the BAP and DoD-TENG tested at room temperature (21° C.) showed an average transmittance of 30.9% and 28.4%, respectively, which are significantly lower than those at elevated temperatures. The large change in transmittance is due to the reversible semicrystalline-to-amorphous transition of the SA and TA moiety, where the semicrystalline state ($T<T_m$) is opaque due to Rayleigh scattering while the amorphous state ($T>T_m$) is transparent. The transmittance of PDMS elastomer (98.8%) and PAAm-LiCl hydrogel (94.9%) are also provided in FIG. 3*f*. The high transparency of the DoD-TENG device on skin can be a useful feature. For instance, the user may choose to keep the low profile of the device, or color it for fashion or expression.

Figure 3G:
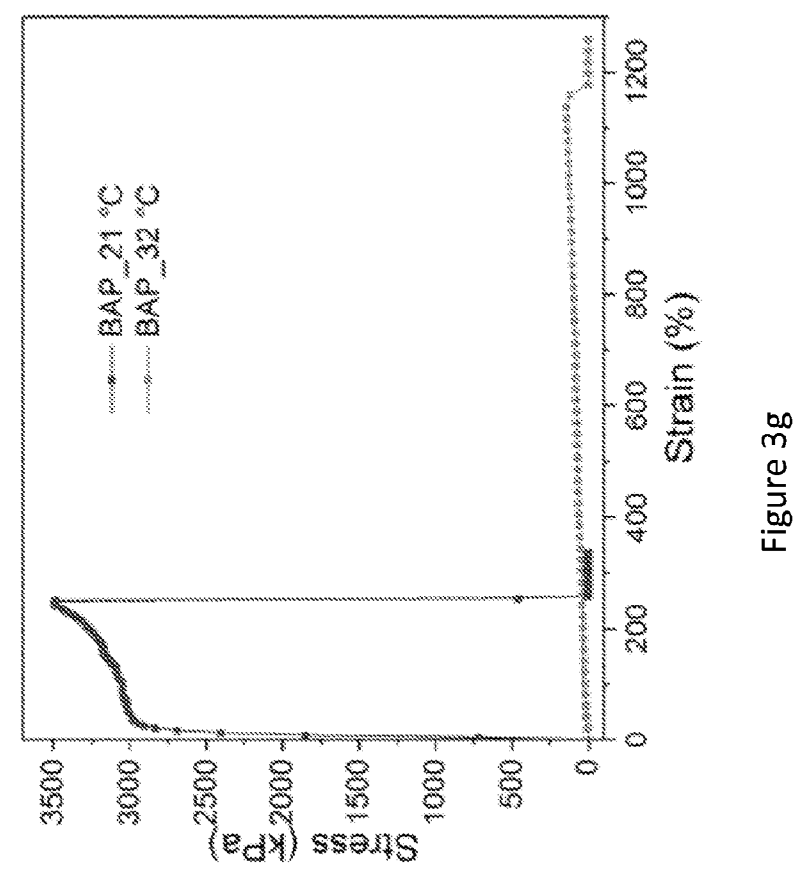
Figure 3:
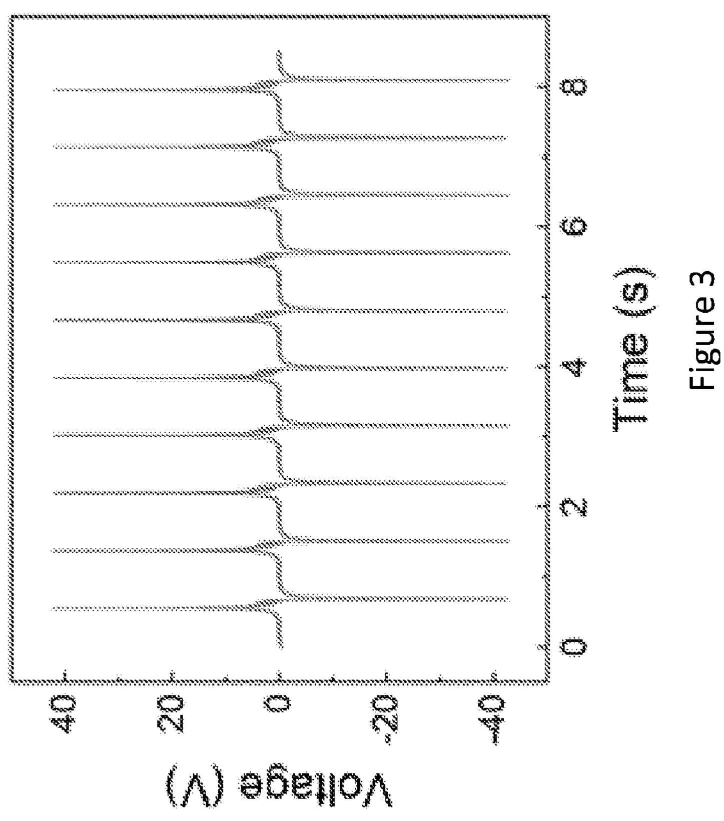
Figure 3:
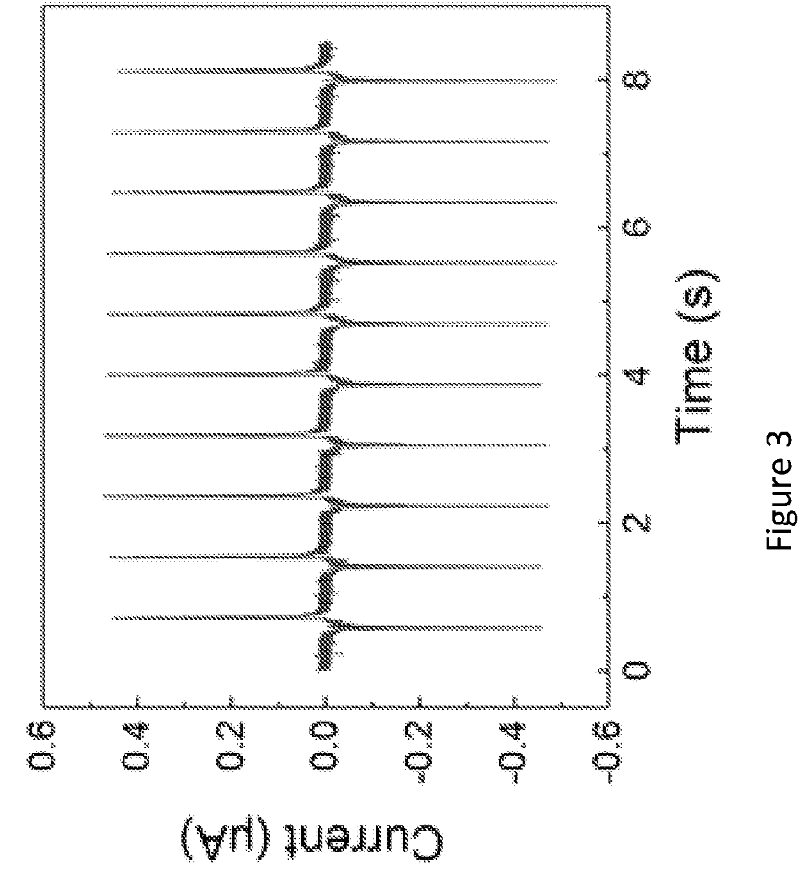
Figure 3:
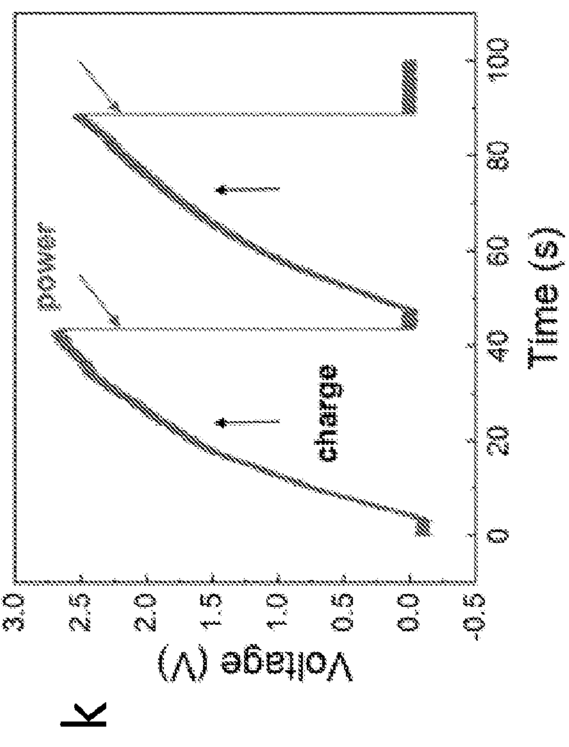
Figure 3:
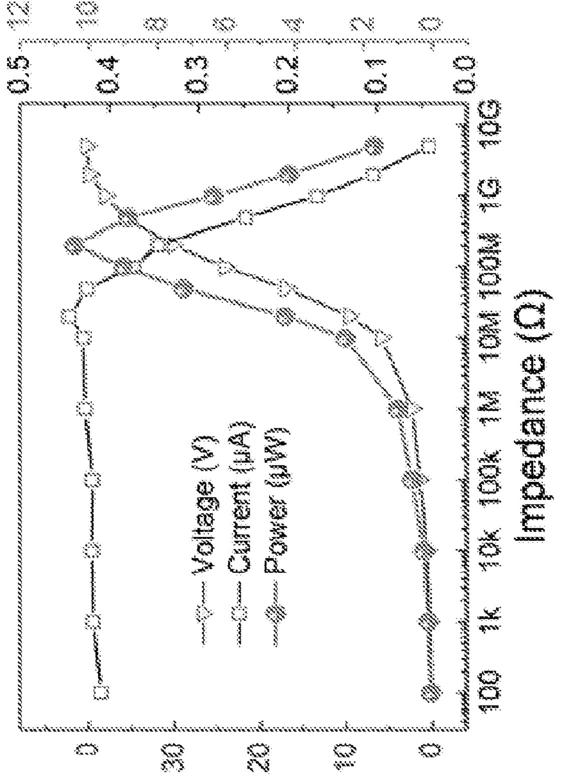
Figure 3:
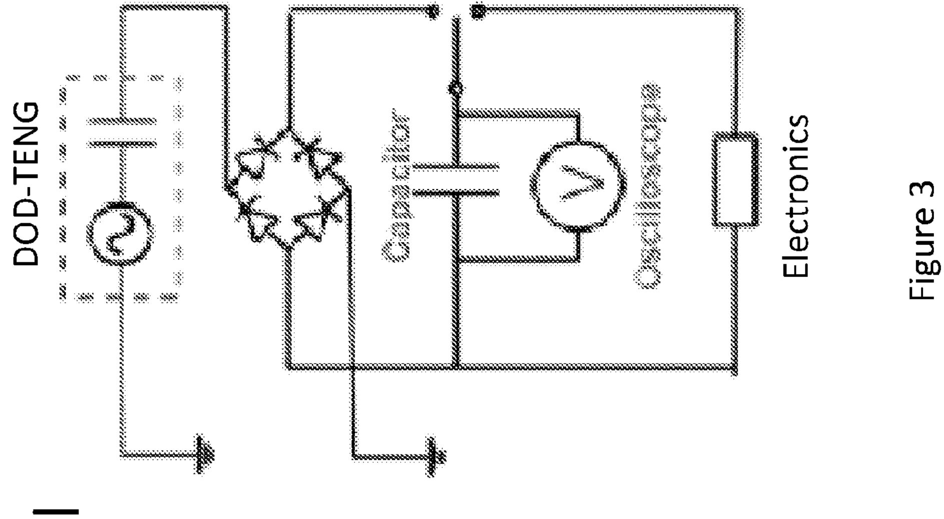
Figure 3:
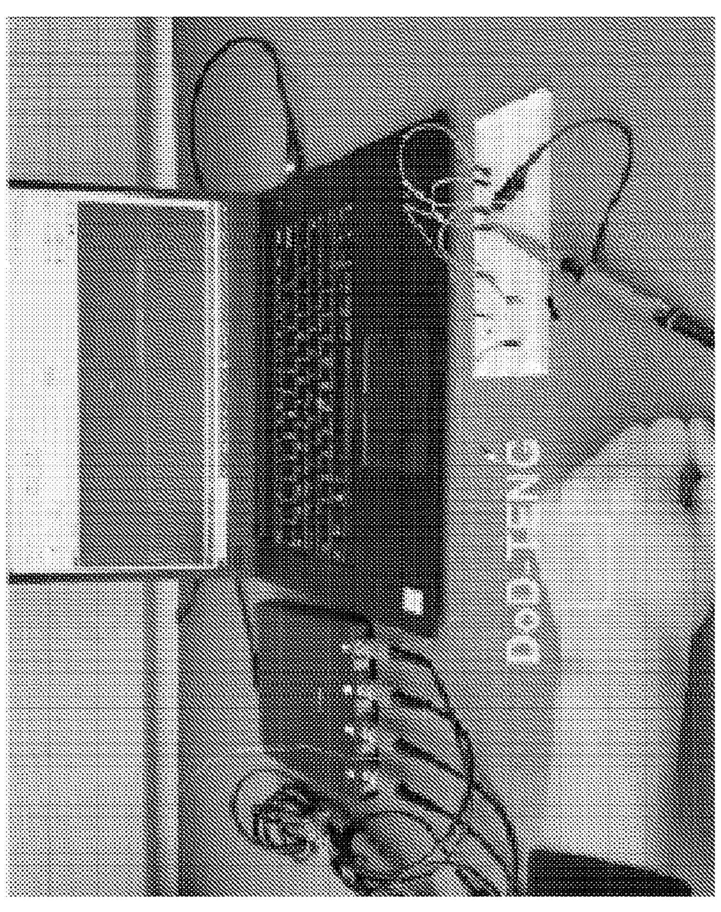
Figure 3:
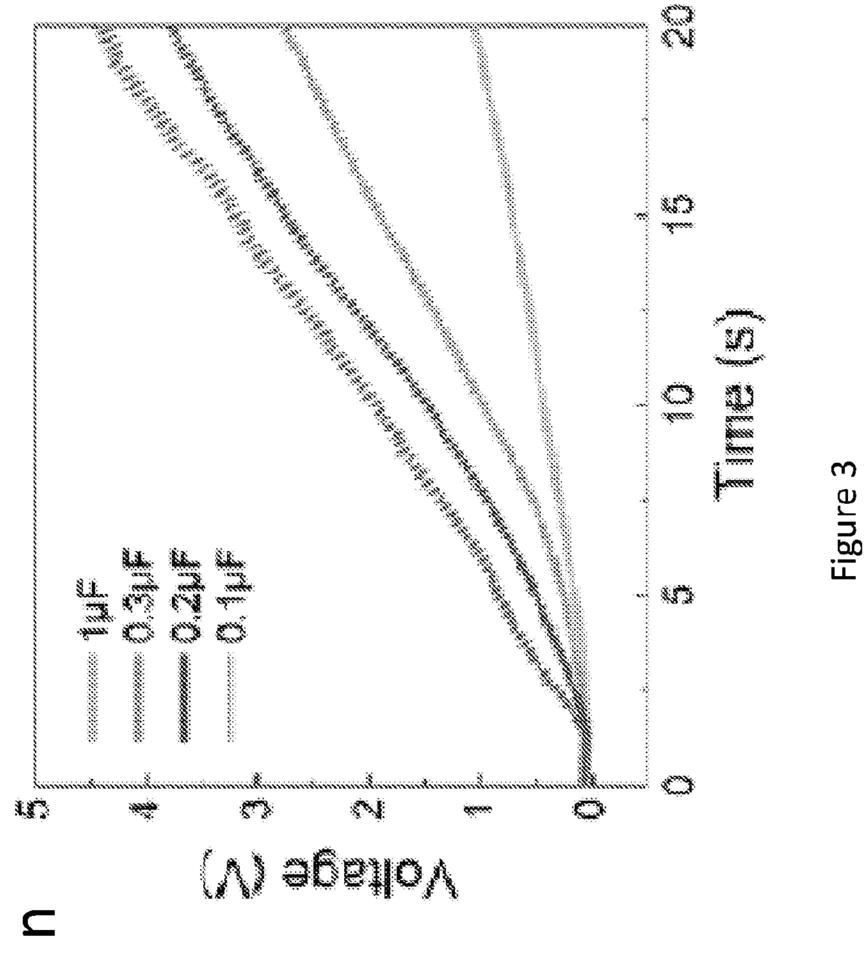
Figure 3:
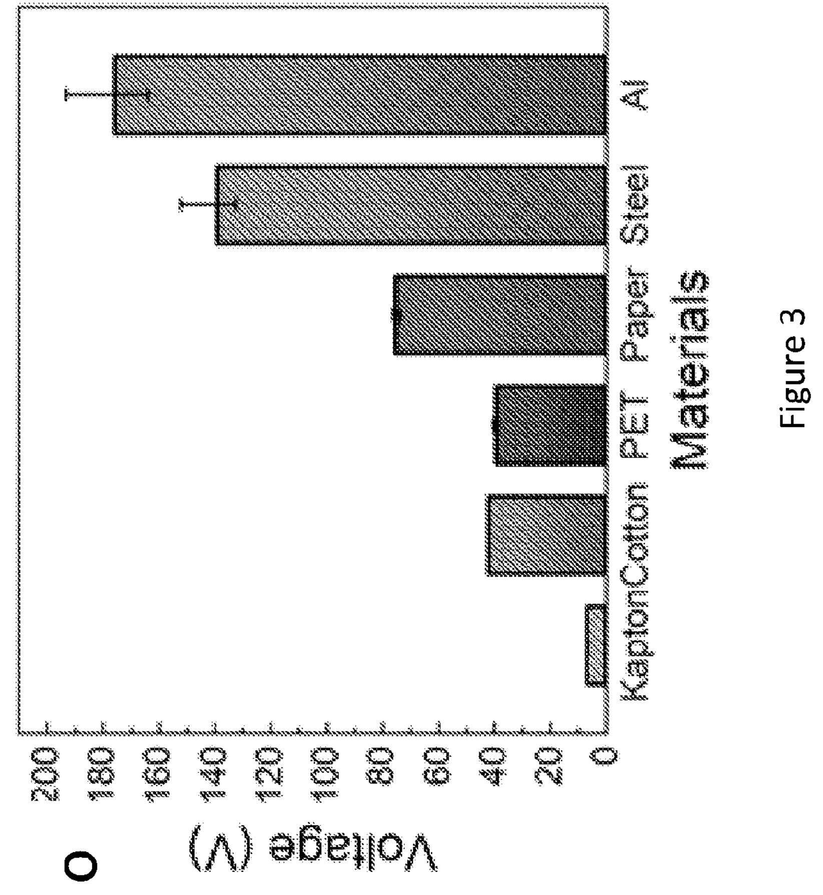
Figure 3:
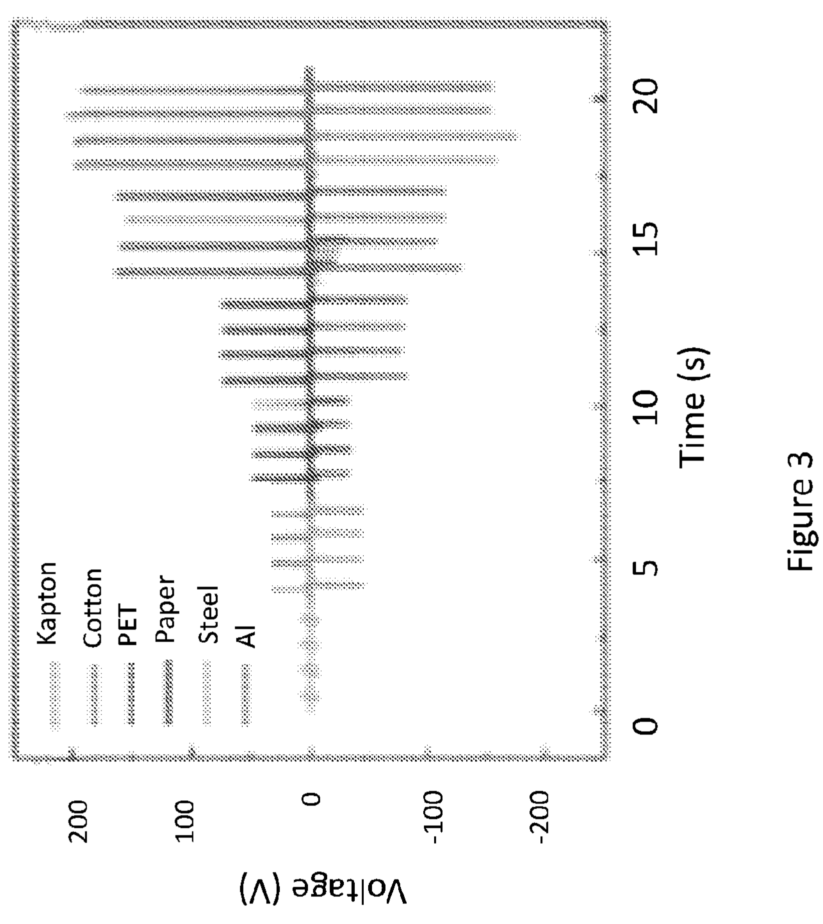
Figure 3:
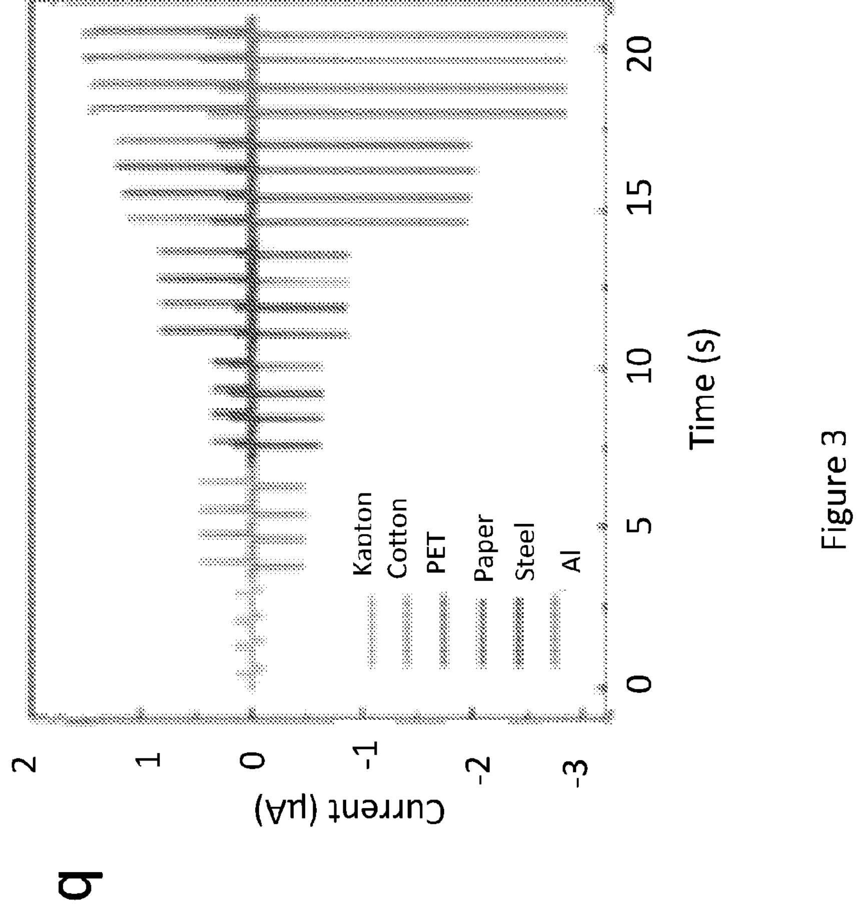
Figure 3:
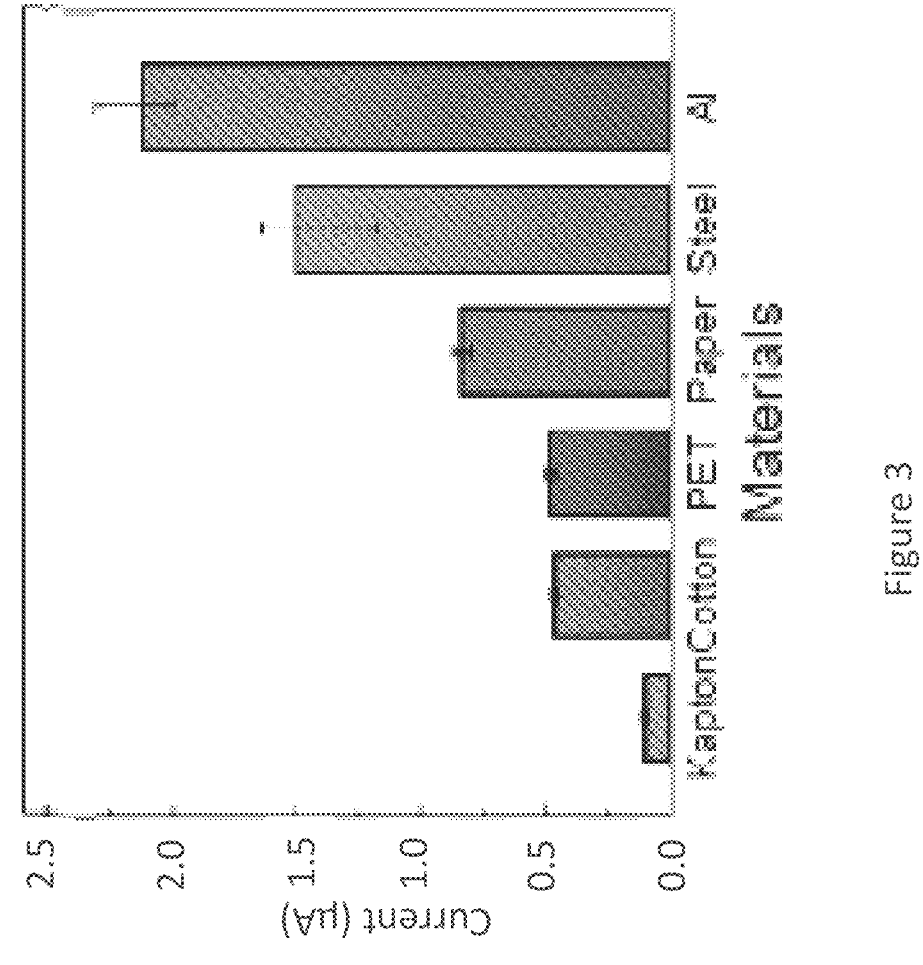

Uniaxial tensile tests of the elastomers used in the device are performed to evaluate the mechanical properties of the DoD-TENGs (FIG. 3*e*). At 32° C., the BAP elastomer had an ultimate tensile stress of 141.2 kPa at a strain of 1138%, while the PDMS elastomer and the PAAm-LiCl hydrogel exhibit an elongation at break at around 1584% and 433%, respectively. The high elongations of each component guarantee the stretchability of DoD-TENG utilized on-skin. It can, therefore, be suggested that ultrahigh stretchability and transparency could be achieved simultaneously when the film is attached on the skin with the temperature above $T_m$. The stress-strain curves of BAP measured at room temperature (21° C.) is also provided in FIG. 3*g*. At room temperature, the BAP reaches a fracture strain at 250%, which is just 22% of that of BAP at 32° C.

In order to test the output signal and electricity generation of the DoD-TENG, periodic contact and separation movements between the device and its contact object is conducted. As demonstrated in FIG. 3*h-i*, when utilizing cloth as the positive triboelectric material, the peak open-circuit voltage and the peak short-circuit current are 42 V and 0.46 μA, respectively, with the input impedance of the oscilloscope being 100 MΩ. The voltage and current waveform depicts a typical triboelectric output with a high signal-to-noise ratio, which shows its ability to be used as high accuracy self-powered sensors. By varying the external resistance, it is observed that the output voltage of the device increased with the increase of external loads with the output current showing a reverse trend according to the Kirchhoff's law. The maximum areal power density output is measured to be 17.37 $mW/m^2$ at an approximately matched impedance of 200 MΩ as shown in FIG. 3*j*.

The charging curves for different capacitors are displayed in FIG. 3*n*. The tests were performed by using a finger to tap a contact area of $3\times2$ $cm^2$ at a frequency of 1 to 2 Hz. FIG. 3*k* shows the real-time charge/discharge curves of capacitors powering a thermistor. The voltage of the capacitor reaches 2.6 V and can later drive the thermistor for about 40 s, which is used to detect the surrounding temperature. By measuring the decay time constant of the discharge curve, the ambient temperature when testing is calculated as 20.98° C. Subsequently, the capacitor can be charged again and can power the thermistor repeatedly.

Due to the feasibility of contact electrification between any two different layers, the DoD-TENG can generate voltage/current outputs from the relative motion with many other materials. Various materials were tested and the corresponding open-circuit voltages were recorded in FIG. 3*o*. The voltage amplitude and polarization depend on the relative ability of a material to lose or gain electrons when in contact with its counterpart adopted in this work i.e. PDMS. FIGS. 3*p-r* show the details of triboelectric output of a variety of tribo-positive materials against the tribo-negative PDMS layer. The results show that the voltage output ranges from 6.9-175.8 V, with the largest value coming from an aluminum thin film. As a result, other materials can also serve as the triboelectric pair with the DoD-TENG, indicating potential applications in other scenarios such as textile based electronics.

Figure 4:
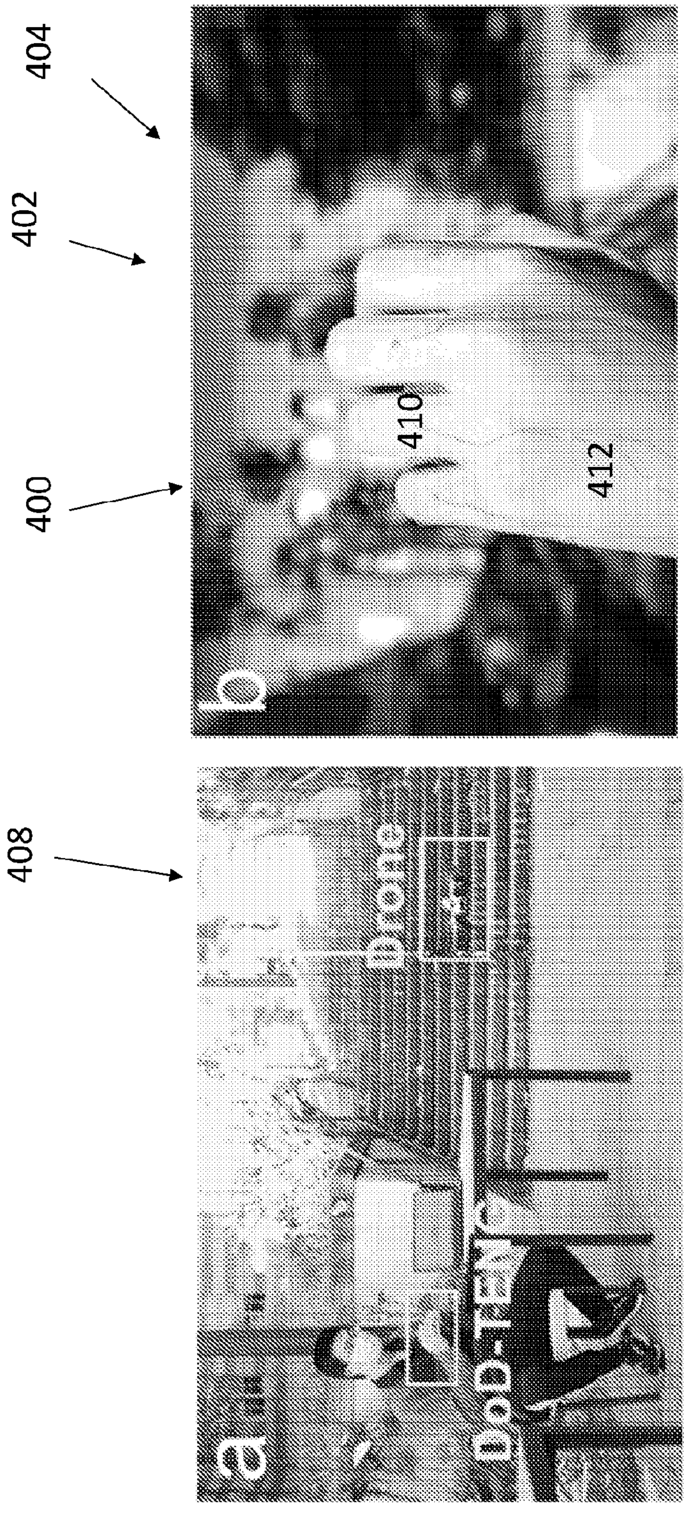
FIG. 4. Application demonstration of the DoD-TENG as human-machine interfaces. *a*) Image of the real-time navigation of a drone with DoD-TENG based sensors as command input. *b*) Image of wearable drone navigator made of four DoD-TENGs attached on human fingers. *c*) Scheme diagram of the DoD-TENG based self-powered drone navigation system, including input, output and processing units. The signal is detected through a multi-channel data acquisition method, and processed via a Matlab script. After processing, real-time statistics are sent to the drone instructing its flight movement. *d*) Screenshot of the graphic user interface on the screen for information feedback. *e*) Voltage waveforms of different inputs and their corresponding flying orders. Index, middle, ring, and little fingers are coded to signal $2^1$, $2^2$, $2^3$, and $2^4$. The motions of the drone are controlled by different commands combination, and the corresponding output voltage waveforms are generated with time sequence of each channel. *f*) Snapshots of the real-time experiments of airborne drone control, which include the commands of taking off, rotation, movement direction, etc., using the WDN developed in this work.
Figure 4:
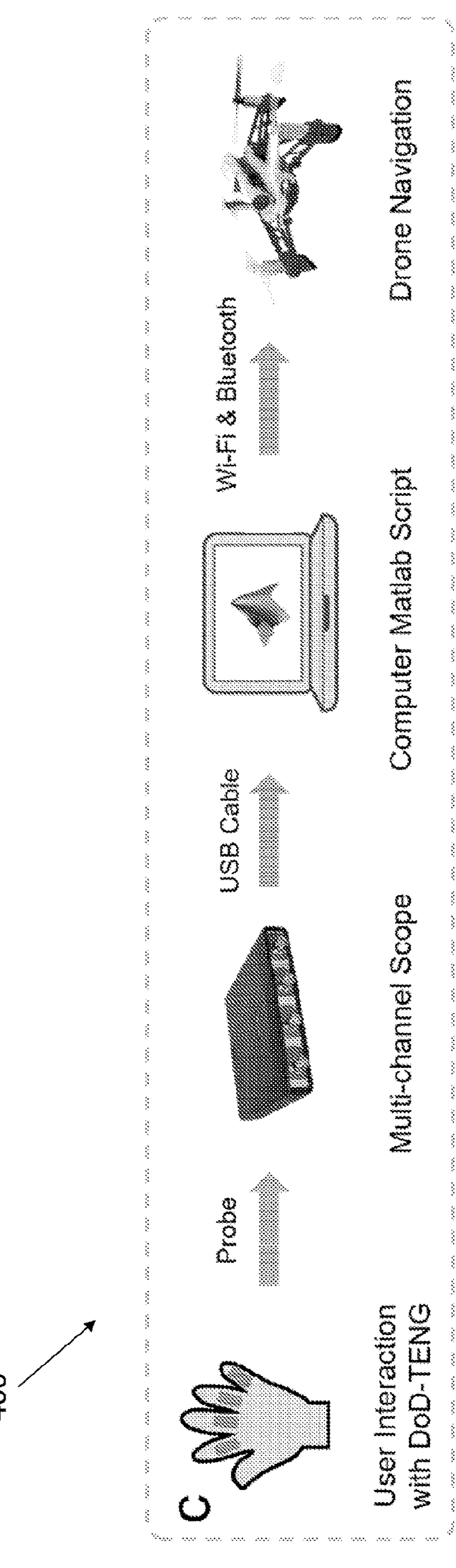
Figure 4:
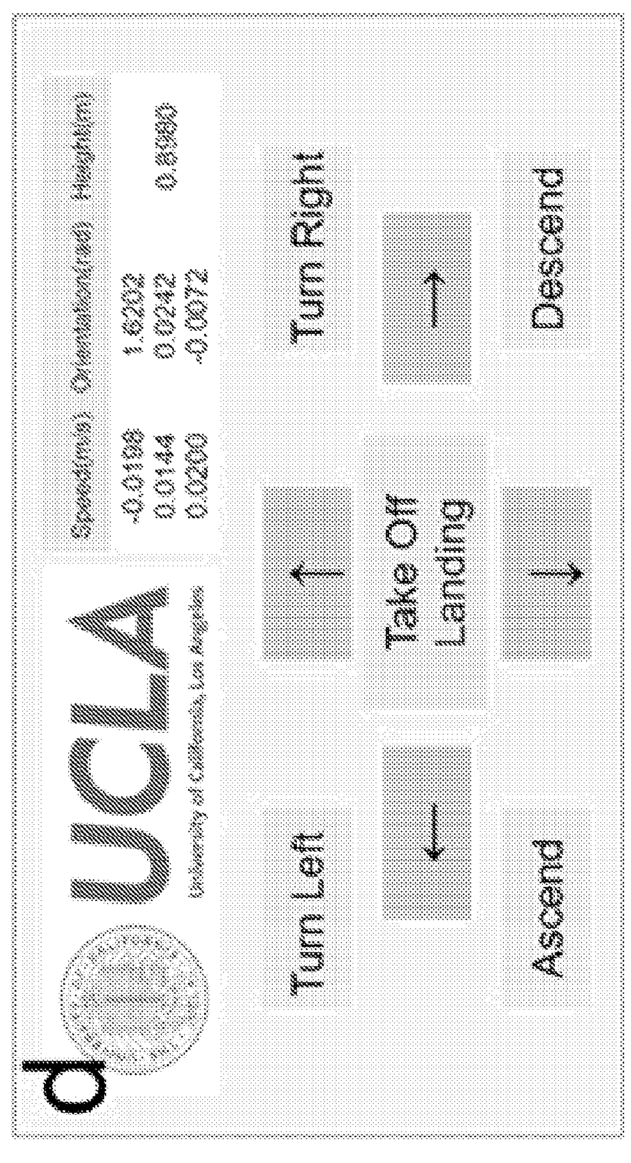
Figure 4:
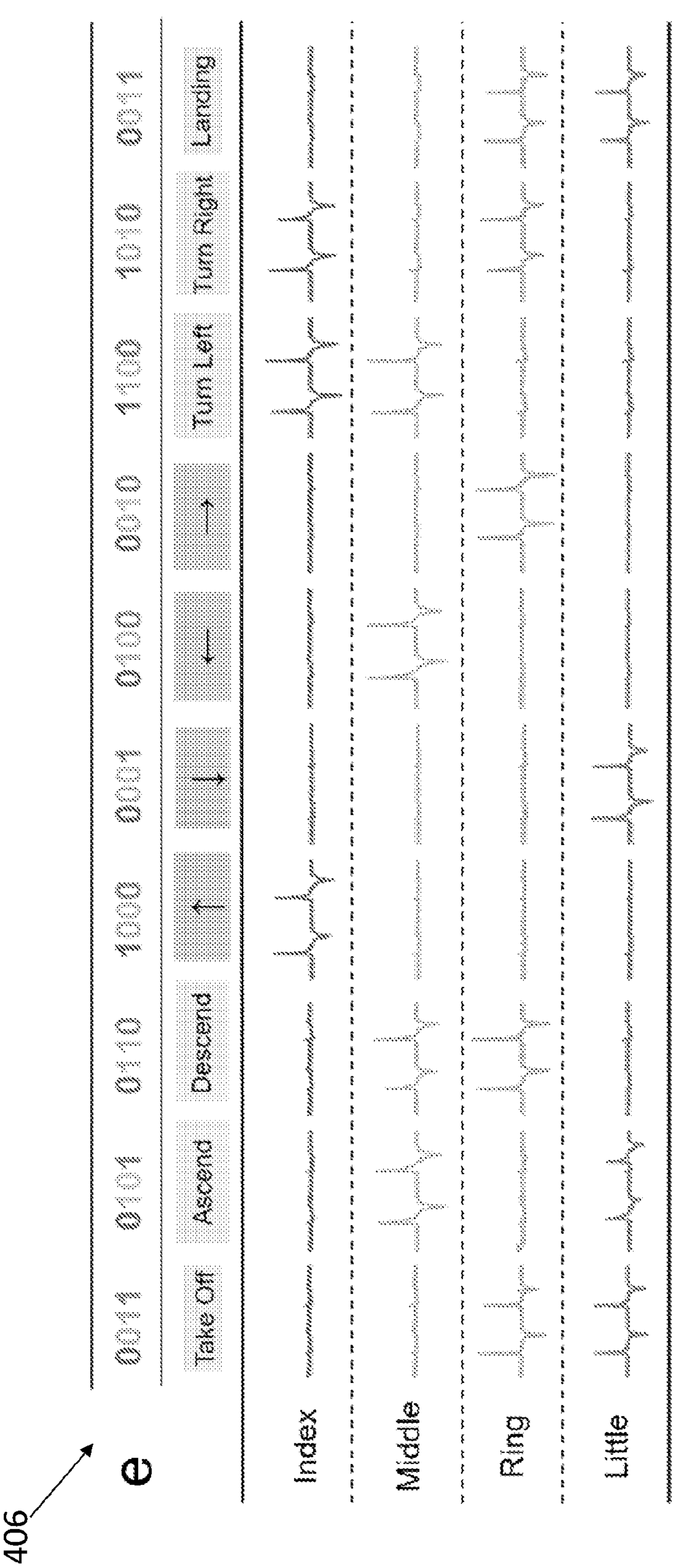
Figure 4F:
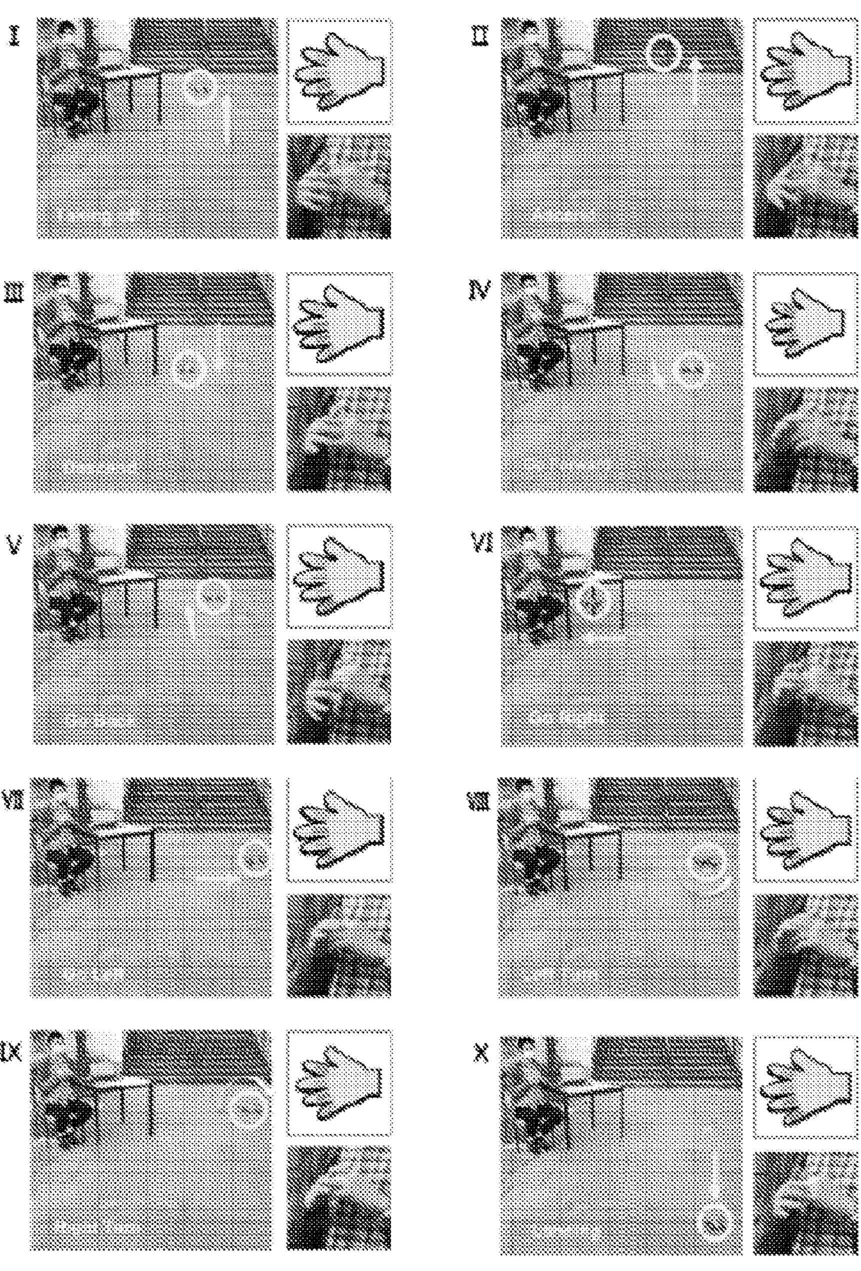

The combination of self-powered sensing ability, stretchability, conformability, and the reversible debonding-on-demand property of the DoD-TENG allowed the fabrication of wearable human-machine interfaces. A wearable drone navigator (WDN) was fabricated via the integration of four DoD-TENGs to provide navigation instruction to a commercial drone (rotations and directions) (FIG. 4*a*). The WDN was attached to the user's fingers (FIG. 4*b*). Index, middle, ring, and little fingers are coded to signal $2^1$, $2^2$, $2^3$, $2^4$ with a microcontroller for real-time communication, respectively. As depicted in FIG. 4*c*, with simple touching interactions on the WDN, the corresponding DoD-TENG will generate an obvious output signal. The signal was detected through a multi-channel data acquisition method, and processed via a Matlab script. After processing, real-time statistics were sent to the drone and instruct its flight movement. The flight information was also displayed on a graphical user interface on the screen for feedback (FIG. 4*d*). The motions of the drone were controlled by different commands, and the corresponding output voltage waveforms with time sequence of each channel are shown in FIG. 4*e*, indicating the feasibility of our sensing system for drone flight manipulation. A value of "0011" was needed to input a "Take Off" order and required a simultaneous touch of the ring finger ($2^3$) and the little finger ($2^4$). For sending a "↑" (Go Forward) order, a value of (1000) was needed, which was given by a single touch of the index finger ($2^1$). Other orders were based on the same mechanism. The various flight movements were successfully carried out as shown in FIG. 4*f*. We conclude that the DoD-TENG based drone navigator can achieve human-machine interaction with high accuracy and low delay, and the device meets the requirements for convenient wearing and accurate manipulation.

The BAP has successfully been explored as a debonding-on-demand (DoD) biocompatible skin adhesive, utilizing the temperature difference between the human body and the ambient environment. The stearyl and tetradecyl long alkyl chains attached to an elastomer network undergoes semicrystalline-to-melt transition between 26° C. and 32° C., resulting in high flowability and large energy dissipation. Topological adhesion to a variety of substrates including artificial skin and human skin are strong at skin temperature, while detaching is made easy by cooling to ambient environment with water and air. The BAP film becomes ultrasoft, conforms tightly on the skin, and adheres strongly. It can easily be detached after by immersing in water for 1 min. A highly stretchable and transparent DoD-TENG was fabricated using a BAP as the DoD substrate, PDMS elastomer as the electrification layer, and PAAm-LiCl hydrogel as the electrode. Based on the single electrode working mode, the E-skin device produces an open circuit voltage of 42 V and a maximum matching peak power density of 17.37 $mW/m^2$. A human-machine interface was also demonstrated for self-powered drone navigation systems. This demonstrates the potential applications of the BAP for a wide range of smart artificial skins, soft robots, and self-powered biomechanical monitoring systems.

Second Example Application: Adhesive for Tissue

Figure 5:
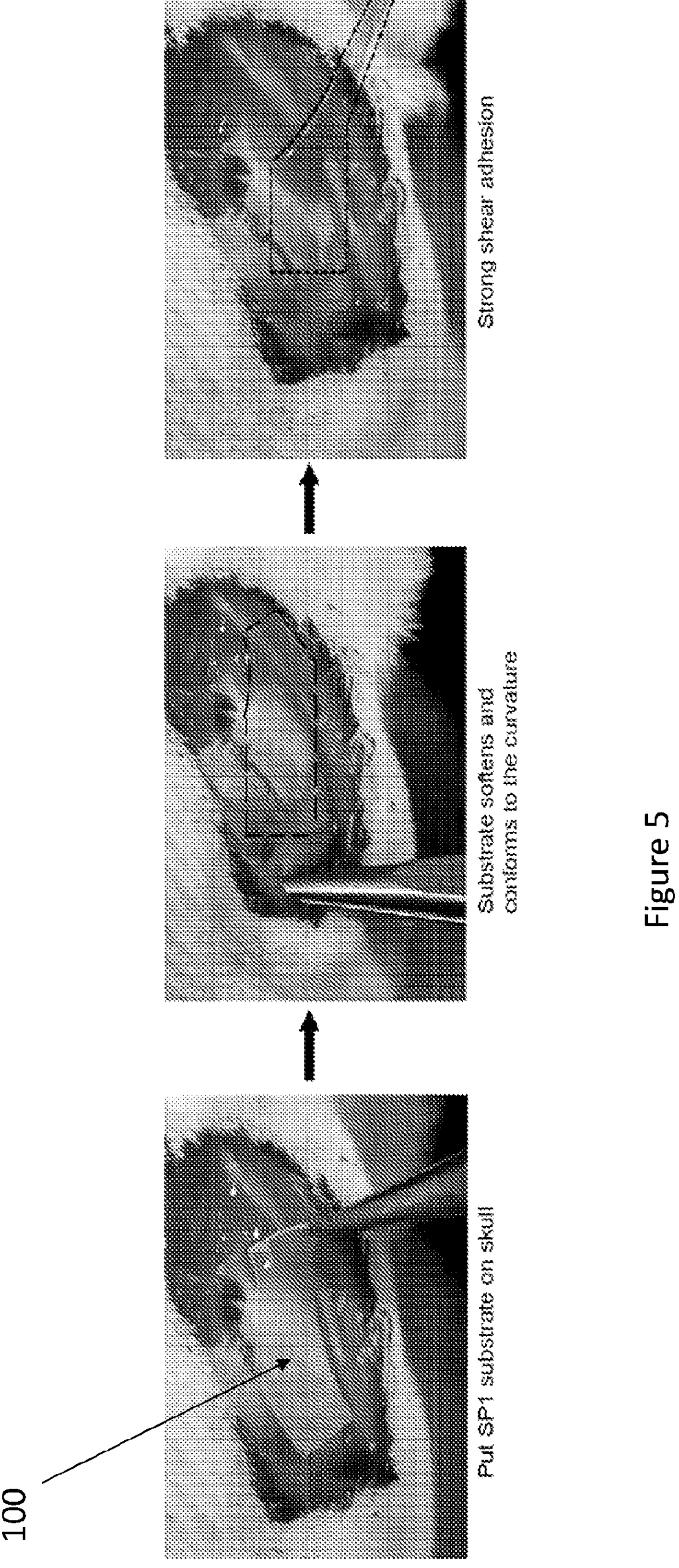
FIG. 5. Demonstration of polymer softening within seconds after attached onto skull of a rat. The film conforms to the curvature with excellent adhesion to prevent from peeling off. Dash line indicates the edge of the polymer.

Strong shear adhesion between the polymer-based electronics and surrounding tissues could prevent offset between the electrodes and tissues during micromotion. Traditional polyimide substrates lack the adhesion to be fixed on tissue. The shear adhesion of the polymer increases sharply as the temperature rises above the transition temperature. Generally, adhesion between two surfaces is strongly dependent on surface roughness and surface chemistry. The softened polymers all show relatively strong adhesion due to their super high softness that ensures maximum surface contact above transition temperature. To demonstrate the strong adhesion of the bioadhesive, we placed the polymer film on a rat's exposed skull, as illustrated in FIG. 5. The film softened within ten seconds and conformed to the curvature of the skull. As we tried to pull it off of the skull, the film tightly adhered to the skull without any observed sliding or displacement. This demonstration clearly shows that the polymer will be a promising substrate for neural interfaces with great resistance against motion-induced offset.

Experimental Section

Figure 6:
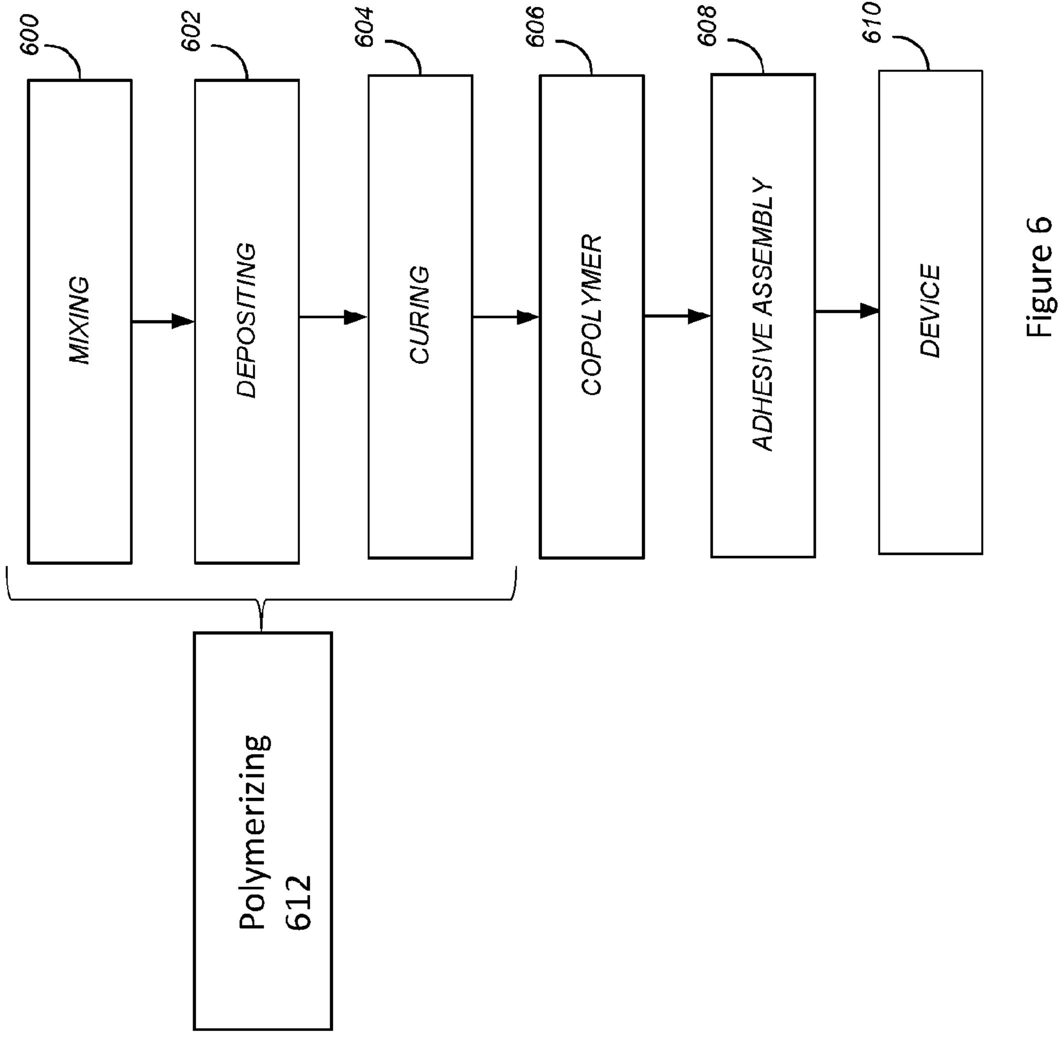
FIG. 6. Flowchart illustrating a method of making a copolymer and adhesive.

FIG. 6 illustrates fabrication of BAP: Block 600 represents the BAP prepared by mixing components (Block 600), depositing the mixture (Block 602); and curing the mixture (Block 604) so as to form a polymer (Block 606). The Example BAP studied in the first example was prepared by mixing SA/TA and UDA oligomers with a weight ratio of 80%:20%. The weight ratio of SA to TA was tuned to investigate the transition temperature. After adding 0.5% of DMPA as a photoinitiator, the entire HA/TA-UDA mixture was sonicated for 30 min before injecting into a glass mold. Then, an UV light irradiation was adopted to initiate the polymerization.

Blocks 608-610 represent optional assembly of the BAP into a device. In one embodiment, the BAP is assembled as an adhesive (Block 608) and then assembled into a device (Block 610).

Fabrication of the PAAm-LiCl hydrogel solution: The ionic hydrogel was synthesized by dissolving 4 g acrylamide (AAm) monomer and 6 g lithium chloride (LiCl) in 10 mL DI water. 0.1 mg/mL of the cross-linker N, Nmethylenebisacrylamide (MBAA) and 5 μL/mL of the photoinitiator 2-hydroxy-2-methylpropiophenone (1173), with respect to the weight of the DI water, were mixed and sonicated for 10 min before use.

Fabrication of DoD-TENG: FIG. 3*b* schematically illustrates the detailed fabrication process of the DoD-TENG. The DoD-TENG consists of the PAAm-LiCl hydrogel solution sandwiched between the bonding/debonding BAP substrate and the negative electrification PDMS layer. BAP precursor is injecting into a rectangular groove mold before UV curing. Then the PAAm-LiCl hydrogel solution was injected into the cavity, and further cured by UV. Then, the PDMS elastomer layer was fabricated by blade coating a well-mixed mixture of commercially available Silicone ELASTOSIL 7670A part A and part B (with a weight ratio of 1:1) on the prepared hydrogel layer. Finally, it was cured at 80° C. for 2 h.

Setup of the Human-Machine Interface Using DoD-TENG for Drone Navigation:

The triboelectric voltage signals generated from the DoD-TENG by tapping fingers are measured by a 4-channel HS4 Scope connected to a computer. The measurement is controlled by a Matlab script with an interval of 0.5 s, and the transmitted signal sections are also analyzed in a real-time manner parallel to the measurement. As a result, input of finger gestures is converted to 10 navigation commands of the drone under the binary coding rule narrated in the article. Then the navigation commands are sent to the drone through Wi-Fi and Bluetooth, with the flight parameters and attitude of the drone fed back and shown on the graphical interface.

Biocompatibility test of BAP film: In a certified A2 biosafety cabinet, BAP films were placed in the standard 24-well cell culture plate after ethanol/UV sterilization. A total of 100,000 NIH3T3 mouse fibroblast cells were seeded in each well and cultured in Dulbecco's modified eagle medium with 10% fetal bovine serum supplemented with penicillin and streptomycin. The cell cultures were placed in 37° C. and 5% $CO_2$ cell incubator for 1 day. Then, LIVE/DEAD cell assay was performed Hoechst 33342 and Ethidium homodimer-III, in which the nuclei of all live or dead NIH3T3 mouse fibroblast cells were stained blue by Hoechst 33342 and dead cells were stained red by EthD-III. Characterization and Measurements:

Mechanical properties were measured on a dynamic mechanical analyzer (TA Instruments RSAIII). Dynamic temperature sweep tests were conducted at a temperature ramping rate of 3° C./min and a frequency of 1 Hz from 21 to 60° C. The stress-strain curves were obtained at room temperature and 32° C. at a stretching rate of 0.25 mm/s. To analyze the flowability of the BAP film, SEM images were taken by a scanning electron microscope (ZEISS Supra 40VP SEM). The peel strength of the BAP film was measured through a 90° peel test with a peeling speed of 50 mm/min using a mechanical testing machine (UniVert, CellScale). The temperature of the BAP film was measured by an infrared camera (ICI 9320P). Live cell microscope (Nikon 90i) is used to observe the fluorescent images of cells cultured with BAP films. UV-Vis spectrometer (SHIMADZU PharmaSpec UV-1700) was used to measure the transmittance spectra of the materials and the DoD-TENG with respect to a glass slide over the range of 400-800 nm. A step motor (LinMot HF01-37) was used to provide the input of mechanical motions. For all testing of energy generation of the DoD-TENG, the pressure (100 kPa), speed (2 m/s), and frequency (1.2 Hz) of the step motor was fixed. The voltage was recorded by a TiePie Handyscope HS4 four channel high resolution oscilloscope, and the current was recorded with a Keithley electrometer 6514. The force applied by the motor was detected by a Mark-10 force gauge.

Device Embodiments

Embodiments of the present invention include, but are not limited to, the following.

1. FIG. 1 illustrates a bioadhesive (e.g., a reversible dry bioadhesive) 100 comprising:
   - a (e.g., long) polymer 102 having a backbone 103 and appendant linear alkyl chains 104, wherein the chains 104 are:
   - (1) crystalline at some temperature below a temperature of skin 106 or living tissue (skin or living tissue temperature);
   - (2) amorphous at the skin or living tissue temperature of the skin 106 or living tissue on which the bioadhesive is applied;
   - (3) the bioadhesive 100 has a first storage modulus (G') less than 2 MPa at the skin or living tissue temperature;
   - (4) the bioadhesive 100 has a second storage modulus at some temperature below the skin or living tissue temperature that is at least 10 times greater than the first storage modulus at the skin or living tissue temperature;
   - (5) the bioadhesive 100 having the skin or living tissue temperature (or a temperature above the skin or living tissue temperature) comprises an adhesive having an adhesion that adheres the bioadhesive to the skin 106 or living tissue;
   - (6) the bioadhesive 100 cooled to a temperature below the skin or tissue temperature has a reduced adhesion or becomes non-adhesive so that the bioadhesive is more easily removable from the skin or living tissue;
   - (7) the bioadhesive is reusable as characterized by the bioadhesive adhering to the skin when the is placed on the skin or living tissue again.

2. Any adhesive assembly 300 comprising the reversible dry bioadhesive of example 1.

3. The reversible dry bioadhesive of Example 1 or 2, wherein:
   - the first storage modulus is less than 1 MPa at the skin or living tissue temperature;
   - the second storage modulus at some temperature below the skin or living tissue temperature is at least 10 times greater than the first storage modulus at the skin or living tissue temperature.

4. The reversible dry bioadhesive of any of the Examples 1-3, wherein:
   - said skin or living tissue temperature is greater than 30° C., but less than 45° C.; said some temperature below skin or living tissue temperature is less than 26° C.

5. The bioadhesive of any of the Examples 1-4, wherein the polymer chains 104 are crosslinked with crosslinks 108 to form an elastomer network 110.

6. The bioadhesive of Example 5, where the crosslinked polymer chains 104 are formed from a liquid formula comprising at least an acrylate monomer or methacrylate monomer, an acrylate methacrylate oligomer, and a polymerization initiator.

7. The bioadhesive of Example 6, where the acrylate oligomer is selected from the group comprising CN9004, CN9021, CN966J75, CN964, urethane diacylate, polyethylene glycol diacrylate, polypropylene glycol diacrylate, hexane diol diacrylate, trimethylolpropane triacrylate, urethane dimethacylate, polyethylene glycol dimethacrylate, polypropylene glycol dimethacrylate, hexanediol dimethacrylate, trimethylolpropane trimethacrylate, and mixtures thereof. In one or more examples, CN9004 comprises a difunctional aliphatic urethane acrylate oligomer, CN9021 comprises a difunctional acrylic ester compound, CN966J75: an aliphatic polyester based urethane diacrylate oligomer blended with 25% isobornyl acrylate, CN964 comprises an aliphatic polyester based urethane diacrylate oligomer, or CN9004, CN9021, CN966J75, and CN964 are as defined by manufacturer Sartomer at https://americas.sartomer.com/.

8. The bioadhesive of any of the Examples 1-7, wherein the appendant linear alkyl chains 104 are selected from the group comprising octadecyl, hexadecyl, tetradecyl, dodecyl, and mixtures thereof, or wherein each, or one or more, of the chains 104 comprise at least one compound selected from octadecyl, hexadecyl, tetradecyl, or dodecyl, or a mixture thereof.

9. The bioadhesive of Example 6 wherein the acrylate or methacrylate monomer is selected from the group comprising octadecyl acrylate, hexadecyl acrylate, tetradecyl acrylate, dodecyl acrylate, octadecyl methacrylate, hexadecyl methacrylate, tetradecyl methacrylate, dodecyl methacrylate, and mixtures thereof, or wherein the acrylate or methacrylate monomer comprises at least one monomer selected from octadecyl acrylate, hexadecyl acrylate, tetradecyl acrylate, dodecyl acrylate, octadecyl methacrylate, hexadecyl methacrylate, tetradecyl methacrylate, dodecyl methacrylate, or a mixture thereof.

10. The bioadhesive of any of the Examples 6-9 wherein the polymerization initiator is a photoinitiator or thermal initiator which may initialize the free radical polymerization of vinyl compounds.

11. The bioadhesive of any of the Examples 6-10, wherein the monomer and oligomer are mixed at a weight ratio in the range of 1:2 and 4:1 (e.g., 1:2≤a:b≤4:1 where a is the weight of the acrylate monomer or methacrylate monomer in the bioadhesive and b is the weight of the acrylate methacrylate oligomer in the bioadhesive).

12. The bioadhesive of any of the Examples 6-11, wherein the acrylate monomer or methacrylate monomer comprises octadecyl acrylate and tetradecyl acrylate mixed at the weight ratio in the range of 1:3 to 4:1 (e.g., 1:3≤c:d≤4:1 where c is the weight of the octadecyl acrylate and d is the weight of the tetradecyl acrylate that are mixed to form the acrylate monomer or methacrylate monomer).

13. The bioadhesive of any of the Examples 6-12, fabricated by a process comprising mixing the monomer, oligomer, and initiator to form a uniform solution (e.g., Block 600 illustrated in FIG. 6), casting, printing, or spin-coating the solution to form a thin layer of the solution (e.g. Block 602 in FIG. 6), and exposing the solution layer to ultraviolet light or heat to cure the solution (e.g., Block 604 in FIG. 6).

14. The bioadhesive of any of the Examples 1-13, wherein the bioadhesive 100 comprising the polymer 102 is coated as a thin layer 1-13 in an adhesive assembly 114, with the bioadhesive layer 112 having a thickness 116 in the range of 10-1000 micrometers.

15. An adhesive assembly 114 comprising the bioadhesive of any of the Examples 1-14, wherein the assembly comprises a biosensor placed on neural interfaces, living tissue, or skin 106.

16. FIG. 3*a* illustrates a biosensor 300 of Example 15, wherein the biosensor is a multi-electrode array, a nerve cuff electrode, a cortical recording or stimulating electrode, a spinal cord recording or stimulating electrode, peripheral recording or stimulating electrode, epidermal electrode, or epidermal sensor, or comprises an electrode 302.

Figure 7A:
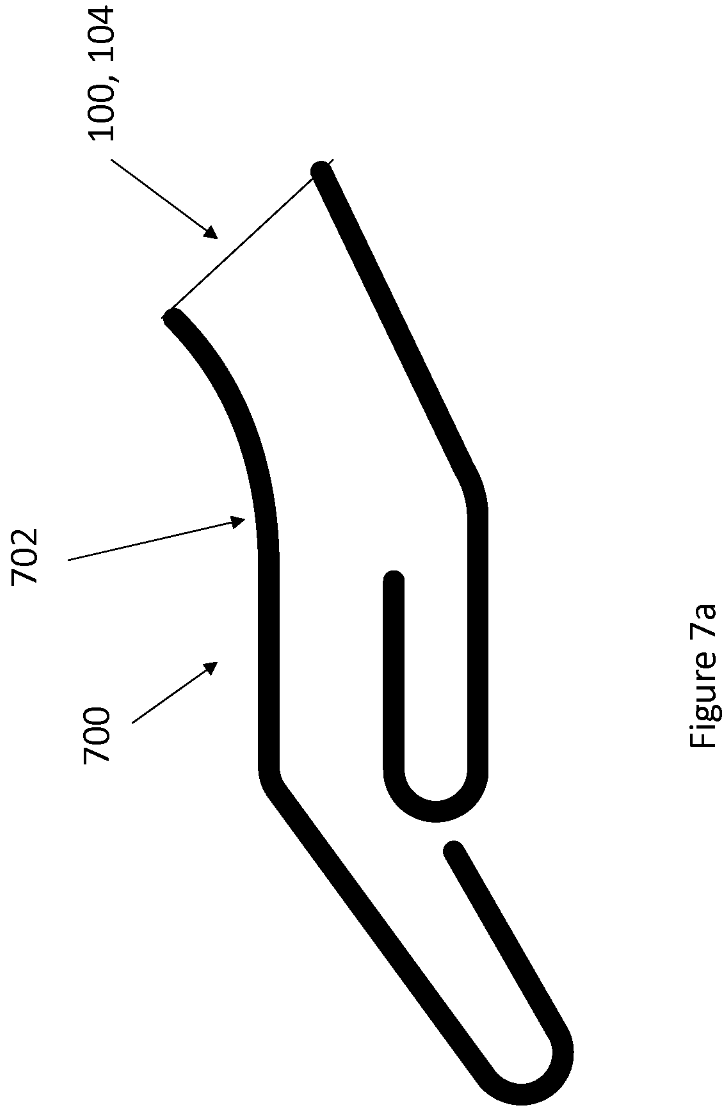
FIG. 7. Example devices including the composition of matter with applications to a hand (a), a stent (b), synthetic tendon (c), human machine interface (d), bandage (e), and anatomical model (f).
Figure 7:
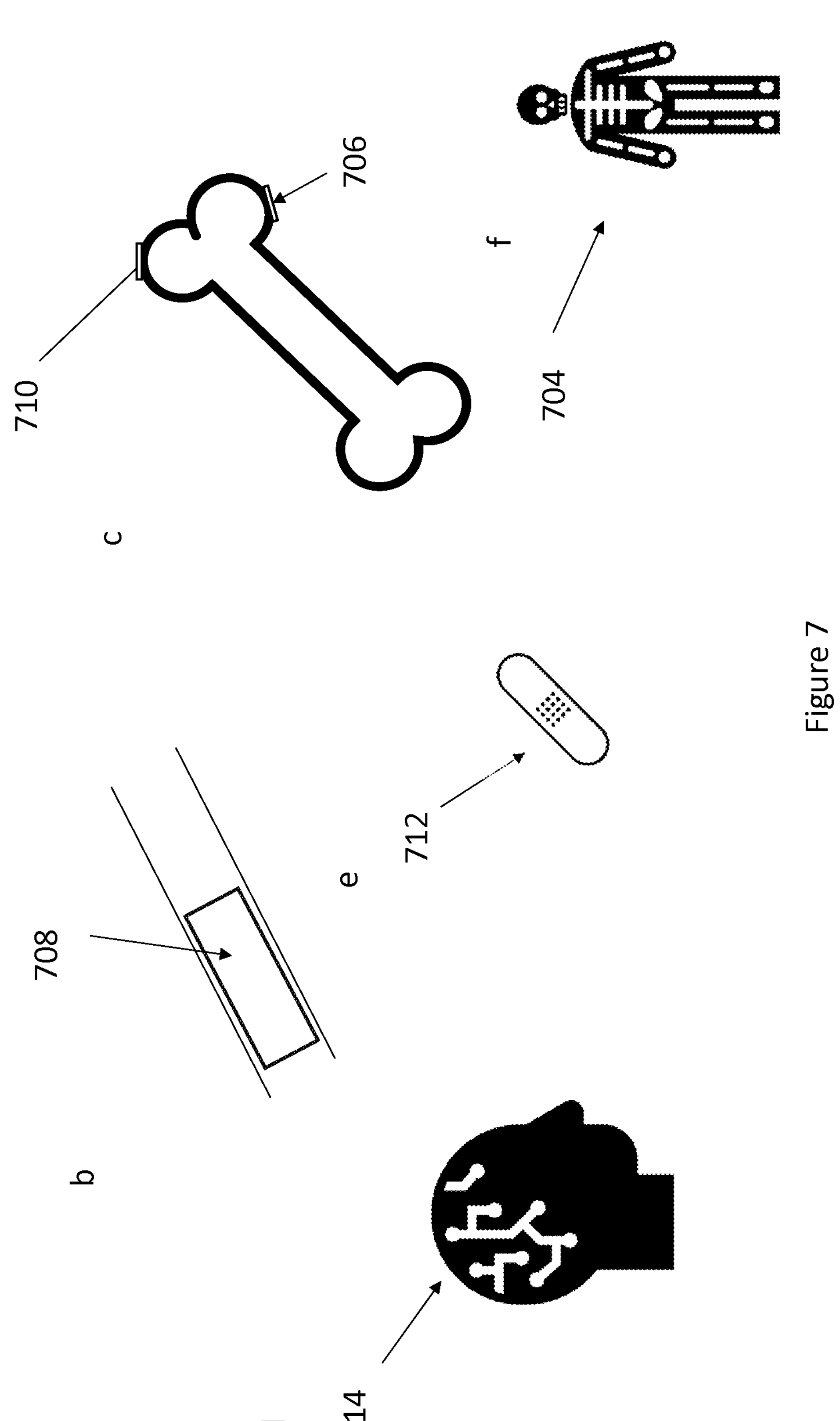

17. FIG. 7 illustrate examples of a prosthetic 700 or plastic surgical implant comprising the bioadhesive 100 of any of the Examples 1-14, to substitute or augment a limb, hand 702, feet, finger, toe, breast, ear, or nose.

18. FIG. 7 further illustrates examples of an anatomical model 704 comprising the bioadhesive of any of the example 1-14, to create tissue phantoms, surgical tools such as but not limited to suture anchors 706, stents 708, valves, catheters, synthetic tendons 710.

19. FIG. 1*b* illustrates a composition of matter 101 useful as an adhesive 100, comprising:
- a bistable adhesive polymer 102 comprising:
- one or more polymer backbones 103;
- side-chains 104 attached to each of the polymer backbones;
- one or more transition temperatures between a crystalline state 152 and an amorphous state 150, wherein:
- the one or more transition temperatures are such that the polymer transitions from the crystalline state to the amorphous state upon physical contact with biological tissue 106 having a temperature higher than the transition temperature; and
- the polymer adheres or attaches to the biological tissue 106 in the amorphous state and can be peeled from the biological tissue when cooled below the transition temperature to the crystalline state.

20. The composition of matter of example 19, wherein:
- the polymer 102 comprises a copolymer including a combination or mixture of a first component 120, a second component 122, a third component 124, wherein:
- the first component has a first transition temperature below the temperature of the biological tissue,
- the second component has a second transition temperature greater than the temperature of the biological tissue,
- the third component has a storage modulus tailoring a polymer storage modulus of the copolymer such that the storage modulus of the third component and the polymer storage modulus are below 2 MPa at the temperature of the biological tissue, and
- the first transition temperature and the second transition temperature are such that the copolymer has the one or more transition temperatures above the first transition temperature but below the temperature of biological tissue.

21. The composition of example 20, wherein the third component (e.g., UTA) does not crystallize and remains as a rubbery material in temperature range from zero to 40 C, and holds all components together in the softened state.

22. The composition of matter of example 20, wherein the copolymer includes at least a fourth component having a fourth transition temperature between the first transition temperature and the second transition temperature (e.g., at or around the temperature of the biological tissue).

23. The composition of matter of example 20, wherein the first component and the second component form crystalline aggregates in the crystalline state and act as a matrix plasticizer for the side-chains in the amorphous state,
- the polymer has lower viscosity so as to flow, conform, and stick to a surface the biological tissue 206 in the amorphous state in response to an external force, and
- the polymer has higher elasticity and higher viscosity in the crystalline state reducing adhesion to the biological tissue and distributing a stretching force over the polymer mitigating against rupturing when the polymer is peeled from the biological tissue 206.

24. FIG. 2*g* further illustrates the composition of matter of any of the examples 19-23, wherein:
- the adhesive 100 comprises a film 200 comprising the polymer 102, and
- the film 200 has a smoother surface 202 interfacing with the biological tissue 106 in the crystalline state and a rougher surface 204 interfacing with the biological tissue 206 in the amorphous state.

25. The composition of matter of any of the examples 19-24, wherein the side chains 104 comprise linear alkyl chains.

26. The composition of matter of any of the examples 20-25, wherein the first component, the second component, and the third component each comprise an acrylate or methacrylate.

27. The composition of matter of any of the examples 20-26, wherein:
- the first component and the second component each independently comprise at least one monomer selected from stearyl acrylate, octadecyl acrylate, hexadecyl acrylate, tetradecyl acrylate, dodecyl acrylate, octadecyl methacrylate, hexadecyl methacrylate, tetradecyl methacrylate, dodecyl methacrylate, and a mixture thereof, and
- the third component comprises at least one oligomer selected from CN9004, CN9021, CN966J75, CN964, urethane diacylate, polyethylene glycol diacrylate, polypropylene glycol diacrylate, hexane diol diacrylate, trimethylolpropane triacrylate, urethane dimethacylate, polyethylene glycol dimethacrylate, polypropylene glycol dimethacrylate, hexanediol dimethacrylate, trimethylolpropane trimethacrylate, and a mixture thereof.

28. The composition of matter of any of the examples 20-27, wherein:

a first weight ratio of the first component to the second component is such that the copolymer has the transition temperature below 32 degrees Celsius, a second weight ratio of the third component to a combination of the first component and the second component is such that the polymer's storage modulus (G') reduces by a factor of at least 1000 in the amorphous state as compared to the crystalline state.

29. The composition of matter of any of the examples 20-28, wherein the first weight ratio is in the range of 1:2 to 4:1 and the second weight ratio is in the range of 1:3 to 4:1. In one or more examples, 1:2≤a:b≤4:1 where a is the in weight of the first component used to form the copolymer 102 and b is the weight of the second component used to form the copolymer 102 and/or 1:3≤c:d≤4:1 where c is the weight of the third component and d is the weight of a combination of the first component and the second component used to form the copolymer 102.

30. The composition of matter of any of the examples 19-29, wherein the side-chains comprise at least one linear alkyl chain selected from an octadecyl, a hexadecyl, a tetradecyl, a dodecyl, and a mixture thereof.

31. The method or composition of matter of any of the examples 19-30, wherein the polymer comprises the structure:

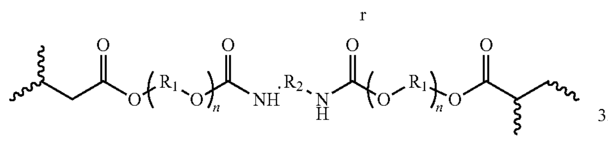

32. The composition of matter of any of the examples 20-31, wherein the first component is stearyl acrylate, the second component is tetradecyl acrylate, and the third component is urethane diacrylate, and the copolymer optionally includes a fourth component hexadecyl acrylate.

33. The composition of matter of any of the examples 19-32, wherein the polymer comprises an adhesive that is reversibly bistable, the adhesive adhering to the biological tissue after at least 10 cycles, each cycle comprising adhering and peeling the polymer from the biological tissue.

34. FIG. 2 illustrates the composition of matter of any of the examples 19-33, wherein the biological tissue 206 comprises skin, human tissue, animal tissue, or bone.

35. FIG. 3 illustrates a device 300 comprising an adhesive including the composition of matter of any of the examples 19-34.

36. FIG. 3, FIG. 7 and FIG. 4 illustrate examples of the device 720 of example 35, wherein the device 720 comprises an electronic skin (E-skin) 402, a bandage, 712, a human machine interface 714, 400, an electrode 302, a prosthetic 700, a surgical implant, a tissue phantom, a surgical suture anchor 706, a stent 708, a valve, a catheter, or a synthetic tendon 710, a biosensor, or an anatomical model.

37. FIG. 4 illustrates the device of example 35 or 36, wherein the device comprises a human machine interface 400 wherein the copolymer 102 reversibly attaches the human machine interface to a body part 404 and touching the human machine interface modulates transmission of an analog or digital signal 406 controlling a machine 408.

38. FIG. 4 illustrates an example of the device of any of the examples 35-37, wherein the machine 408 comprises a drone and the touching controls a motion of the drone.

39. The device of example 37 or 38, wherein the body part comprises one or more fingers 410, 412 or a hand.

40. FIG. 6 illustrates a method of making a composition of matter useful as a bioadhesive 100, comprising:

polymerizing 612 a combination of a first component 120, a second component 122, and a third component 124 to form a copolymer 102, wherein:

the first component has a first transition temperature below the temperature of the biological tissue, the second component has a second transition temperature greater than the temperature of the biological tissue, the third component has a storage modulus tailoring a polymer storage modulus of the copolymer such that the storage modulus of the third component and the polymer storage modulus are below 2 mega Pascals (MPa) at the temperature of the biological tissue, and the first transition temperature and the second transition temperature are such that the copolymer has the one or more transition temperatures above the first transition temperature but below the temperature of biological tissue.

41. FIG. 6 illustrates the method of example 40, wherein the polymerizing includes:

mixing (Block 600) the first component, the second component, and the third component with a polymerization initiator in a solution; and curing (Block 604) the solution to form the copolymer (Block 604). The copolymer can optionally then be deposited in an adhesive assembly/bio adhesive (Block 606) and then a device (Block 608).

42. The method or composition of matter of any of the examples 20-41, wherein the first component, the second component, and the third component are crosslinked.

43. The method of any of the examples 40-41 used to make the composition of matter of any of the examples 19-39.

44. The method or composition of matter of any of the examples 1-43, wherein the adhesion of the polymer in the amorphous state is increased by a factor of at least 5 as compared to in the crystalline state, as measured by a 90 degree peeling test.

45. The method or composition of matter of example 44, wherein:

the peeling strength of the polymer from artificial skin is at least 50 N/m in the amorphous state, as measured in a 90 degree peeling test, and the peeling strength of the polymer from the artificial skin is less than 10 N/m in the crystalline state, as measured in the 90 degree peeling test.

46. The copolymer 102 or polymer of one or more of the examples 1-45 comprising homopolymers comprising stearyl acrylate (SA), hexadecyl acrylate (HDA), and tetradecyl acrylate (TA), wherein the homopolymers' transition temperatures are above skin temperature, around skin temperature, and below, respectively. The transition temperature of a mixture is between those of the three homopolymers (between the highest Tm and lowest Tm of the three homopolymers). In one or more examples, the transition temperature of the mixture is an average of the Tm of the three homopolymers.

47. The copolymer or polymer of any of the examples 1-46, wherein the first component 120, the second component 122, and the third component 124 combine synergistically to form the copolymer 102 having the one or more transition temperatures wherein the copolymer transitions from the crystalline state to the amorphous state upon physical contact with biological tissue 106 having a temperature higher than the transition temperature and the polymer adheres or attaches to the biological tissue 106 in the amorphous state and can be peeled from the biological tissue when cooled below the transition temperature to the crystalline state.

48. The copolymer, adhesive, or composition of matter of any of the examples 1-47, wherein the storage modulus G' is a measure of the stored energy in dynamic mechanical analysis, representing the material's ability to store energy elastically.

49. Textile or clothing or a wearable device including the composition of matter or adhesive or any of the examples 1-48.

Advantages and Improvements

Adhesives are widely used; including, but not limited to, packaging, textiles, household needs, fasteners, medicine, and wearable electronics. Adhesives that bond to biological tissues or skin, for example, medical tapes, wound or surgical dressings, bioelectrical sticker, have versatile applications to adhere medical devices such as sensors, electrodes, and electrical power supply, and transdermal delivery devices. For such bioadhesives, fast and efficient adhesion formation, strong and conformal bonding, high biocompatibility, good mechanical match with skins and tissues, and painless detachment are required in practical usage. It is often necessary to trade high levels of adhesion to ensure that the adhered assembly do not fall off from the substrate to reduce trauma, damage, or irritation during use and/or removal of the adhesive assembly. Therefore, reversible debonding-on-demand (DoD) adhesive is demanded that offers strong adhesion and may be removed safely without causing damage to the substrate. Several different stimuli-responsive adhesives have been reported where the easy removal of the adhesives are triggered by ultraviolet light exposure, treatment with a chemical, application of a strong magnetic field, and external heating. Most of these reversible adhesives are not suitable as reversible bioadhesive either because the trigger is harmful or not readily available. Heat-induced debonding may be efficient, accessible, contactless, remotely stimulated, if the required temperature is not too high to cause skin or tissue damage.

U.S. Pat. No. 2018/0179425 A1 provides a reversible adhesive comprising two sets of polymer fibers comprising polyhedral oligomeric silsesquioxane-containing thermoplastic polyurethane elastomer and poly(ε-caprolactone), respectively. The adhesive is heated to melting point around 54° C.-56° C. to soften the adhesive mat to conform on substrate. An external heating source is required for its operation.

U.S. Pat. No. 2020/0270488 A1 provides a nanocomposite having two temperature-sensitive components: the melting of the cellulose nanocrystals at ca. 75° C. dynamic bonding behavior of disulfide bonds at ca. 150° C. Two levels of adhesion are obtained at about 80° C. for relatively weak bonding and at 150° C. for relatively strong adhesion. These temperatures are too high application, and an external heating source is required for its operation.

U.S. Pat. No. 10,751,223 B1 provides bandage removal system comprising an adhesive, an adhesive solvent, and an adhesive solvent release agent. The adhesive solvent release agent includes microbeads that contain a composition that liquefies at a temperature between 42° C. and 46° C. An air reactive compound is included in the adhesive system to trigger the release of the solvent and the removal of the adhesive. This bandage has a rather complex structure, and it is not reusable after the removal.

U.S. Pat. No. 7,399,800 B2 provides a switchable pressure-sensitive adhesives comprising an elastomer and a crystallizable abietic acid derivative as tackifier. When heated above the melting temperature of the tackifier, the adhesive loses bonding strength and may be peeled off from the substrate. The use of small molecule tackifier may leave residue on the substrate. The tackifier may leach out of the adhesive over time.

Embodiments of the present invention provide a reversible and reusable dry bioadhesive which allows an adhesive assembly to be attached to skin and living tissues to provide strong adhesion, may be readily detached by cooling to a mildly low temperature, and may be reattached to skin and living tissues to provide strong adhesion.

The reversible and reusable dry bioadhesive according to embodiments described herein comprises a polymer having appendant linear alkyl chains which are crystalline at a cooled temperature and melt at the body temperature. At the body temperature, the adhesive is tacky, soft, and conforms on the substrate to form strong adhesion and good mechanical compliancy with skin and tissue substrate. When it is cooled to below body temperature, such as below 25° C., the adhesive becomes relatively stiff, non-tacky and easily removable from the skin and adhesion again when placed on skin and living tissue.

REFERENCES

The following references are incorporated by reference herein.

[1] W. Ding, A. C. Wang, C. Wu, H. Guo, Z. L. Wang, *Adv. Mater. Technol.* 2019, 4, 1800487.

[2] J.-W. Jeong, W.-H. Yeo, A. Akhtar, J. J. S. Norton, Y.-J. Kwack, S. Li, S.-Y. Jung, Y. Su, W. Lee, J. Xia, H. Cheng, Y. Huang, W.-S. Choi, T. Bretl, J. A. Rogers, *Adv. Mater.* 2013, 25, 6839.

[3] M. A. Lebedev, M. A. L. Nicolelis, *Trends Neurosci.* 2006, 29, 536.

[4] A. Chortos, J. Liu, Z. Bao, *Nat. Mater.* 2016, 15, 937.

[5] J. C. Yang, J. Mun, S. Y. Kwon, S. Park, Z. N. Bao, S. Park, *Adv. Mater.* 2019, 31.

[6] D.-H. Kim, N. Lu, R. Ma, Y.-S. Kim, R.-H. Kim, S. Wang, J. Wu, S. M. Won, H. Tao, A. Islam, K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, J. A. Rogers, *Science* 2011, 333, 838.

[7] I. Hwang, H. N. Kim, M. Seong, S.-H. Lee, M. Kang, H. Yi, W. G. Bae, M. K. Kwak, H. E. Jeong, *Adv. Healthcare Mater.* 2018, 7, 1800275.

[8] X. Peng, K. Dong, C. Ye, Y. Jiang, S. Zhai, R. Cheng, D. Liu, X. Gao, J. Wang, Z. L. Wang, *Sci. Adv.* 2020, 6, 9624.

[9] K. Meng, S. Zhao, Y. Zhou, Y. Wu, S. Zhang, Q. He, X. Wang, Z. Zhou, W. Fan, X. Tan, J. Yang, J. Chen, *Matter* 2020, 2, 896.

[10] C. Qian, L. Li, M. Gao, H. Yang, Z. Cai, B. Chen, Z. Xiang, Z. Zhang, Y. Song, *Nano Energy* 2019, 63, 103885.

[11] H. Wu, Z. Su, M. Shi, L. Miao, Y. Song, H. Chen, M. Han, H. Zhang, *Adv. Funct. Mater.* 2018, 28.

[12] Z. L. Wang, *Mater. Today* 2017, 20, 74.

[13] C. Wu, A. C. Wang, W. Ding, H. Guo, Z. L. Wang, *Adv. Energy Mater.* 2019, 9, 1802906.

[14] D.-M. Drotlef, M. Amjadi, M. Yunusa, M. Sitti, *Adv. Mater.* 2017, 29, 1701353.
[15] S. Chun, D. W. Kim, S. Baik, H. J. Lee, J. H. Lee, S. H. Bhang, C. Pang, *Adv. Funct. Mater.* 2018, 28, 1805224.
[16] M. B. Novikov, T. A. Borodulina, S. V. Kotomin, V. G. Kulichikhin, M. M. Feldstein, *The Journal of Adhesion* 2005, 81, 77.
[17] H. Yuk, T. Zhang, S. Lin, G. A. Parada, X. Zhao, *Nat. Mater.* 2016, 15, 190.
[18] J. Li, A. D. Celiz, J. Yang, Q. Yang, I. Wamala, W. Whyte, B. R. Seo, N. V. Vasilyev, J. J. Vlassak, Z. Suo, D. J. Mooney, *Science* 2017, 357, 378.
[19] Q. Liu, G. Nian, C. Yang, S. Qu, Z. Suo, *Nat. Commun.* 2018, 9, 846.
[20] J. Saiz-Poseu, J. Mancebo-Aracil, F. Nador, F. Busque, D. Ruiz-Molina, *Adv. Mater.* 2019, 58, 696.
[21] X. Chen, *Adv. Mater.* 2017, 1, 1600029.
[22] X. Chen, H. Yuk, J. Wu, C. S. Nabzdyk, X. Zhao, *Proc. Natl. Acad. Sci. U.S.A.* 2020, 117, 15497.
[23] Y. Gao, K. Wu, Z. Suo, *Adv. Mater.* 2019, 31, 1806948.
[24] D. K. Hohl, C. Weder, *Adv. Opt. Mater.* 2019, 7, 1900230.
[25] N. Kim, H. Kang, J.-H. Lee, S. Kee, S. H. Lee, K. Lee, *Adv. Mater.* 2015, 27, 2317.
[26] J. Yang, R. Bai, Z. Suo, *Adv. Mater.* 2018, 30, 1800671.
[27] L. Xue, A. Kovalev, K. Dening, A. Eichler-Volf, H. Eickmeier, M. Haase, D. Enke, M. Steinhart, S. N. Gorb, *Nano Lett.* 2013, 13, 5541.
[28] D.-M. Drotlef, P. Blümler, A. del Campo, *Adv. Mater.* 2014, 26, 775.
[29] J. Eisenhaure, S. J. P. Kim, *Polymers* 2014, 6, 2274.
[30] Z. Ren, W. Hu, C. Liu, S. Li, X. Niu, Q. Pei, *Macromolecules* 2016, 49, 134.
[31] C. Creton, *MRS Bull.* 2003, 28, 434.
[32] A. R. C. Baljon, M. O. Robbins, *Science* 1996, 271, 482.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A composition of matter, comprising:
a bistable adhesive polymer comprising:
one or more polymer backbones;
side-chains attached to each of the polymer backbones, wherein:
the side-chains comprise linear alkyl chains,
the side-chains comprise a first component having a first transition temperature and a second component having a second transition temperature;
the transition temperatures are for phase transitions between a crystalline state and an amorphous state, wherein:
the bistable adhesive polymer comprises polymer chains that are crosslinked with a third component to form an elastomer network;
the first and second transition temperatures are such that the bistable adhesive polymer transitions from the crystalline state to the amorphous state upon physical contact with a temperature higher than the transition temperature of the bistable adhesive polymer determined by the first and second transition temperatures; and
the bistable adhesive polymer adheres or attaches to a substrate in the amorphous state and can be peeled from the substrate when cooled below the transition temperature to the crystalline state.

2. The composition of matter of claim 1 comprising a bioadhesive, wherein:
the substrate comprises skin or living tissue having a skin or living tissue temperature,
the bistable adhesive polymer:
comprises crystalline regions at a temperature below the skin or the living tissue temperature, and
is amorphous when applied on the skin or living tissue at the skin or living tissue temperature;
the bioadhesive has a first storage modulus less than 2 MPa at the skin or the living tissue temperature;
the bioadhesive, comprising the bistable adhesive polymer in the amorphous state, adheres with the skin or living tissue;
the bioadhesive has a second storage modulus, at some temperature below the skin or the living tissue temperature, that is at least 10 times greater than the first storage modulus at the skin or living tissue temperature;
the bioadhesive is removable from the skin or living tissue by cooling to below the skin or the living tissue temperature; and
after removal from the skin or living tissue, the bioadhesive adheres to the skin or living when it is placed again on the skin or living tissue.

3. The bioadhesive of claim 2, wherein the bioadhesive:
has the first storage modulus less than 1 MPa at the skin or living tissue temperature; and
has the second storage modulus at a temperature below the skin or living tissue temperature that is at least 10 times greater than the first storage modulus at skin or living tissue temperature.

4. The bioadhesive of claim 2, wherein:
said skin or living tissue temperature is greater than 30° C., but less than 45° C.; and said temperature below-the skin or living tissue temperature is less than 26° C.

5. The composition of matter of claim 1, where the polymer chains are formed from a liquid formula comprising at least an acrylate monomer or a methacrylate monomer, an oligomer comprising an acrylate oligomer or a methacrylate oligomer, and a polymerization initiator.

6. The composition of matter of claim 5, wherein the acrylate oligomer comprises at least one of urethane diacylate, polyethylene glycol diacrylate, polypropylene glycol diacrylate, hexane diol diacrylate, trimethylolpropane triacrylate, urethane dimethacylate, polyethylene glycol dimethacrylate, polypropylene glycol dimethacrylate, hexanediol dimethacrylate, trimethylolpropane trimethacrylate, or a mixture thereof.

7. The composition of matter of claim 1, wherein the linear alkyl chains comprise at least of octadecyl, hexadecyl, tetradecyl, dodecyl, or a mixture thereof.

8. The composition of matter of claim 5, wherein the acrylate monomer or the methacrylate monomer comprises at least one of octadecyl acrylate, hexadecyl acrylate, tetradecyl acrylate, dodecyl acrylate, octadecyl methacrylate, hexadecyl methacrylate, tetradecyl methacrylate, dodecyl methacrylate, or a mixture thereof.

9. The composition of matter of claim 5, wherein the polymerization initiator is a photoinitiator or thermal initiator which may initialize a free radical polymerization of a vinyl compound.

10. The composition of matter of claim 5, wherein the monomer and the oligomer are mixed at a weight ratio in the range of 1:2 to 4:1.

11. The composition of matter of claim 8, wherein the acrylate monomer or the methacrylate monomer comprises octadecyl acrylate and tetradecyl acrylate mixed at a weight ratio in the range of 1:3 to 4:1.

12. The composition of matter of claim 5, fabricated by a process comprising:

mixing the monomer, oligomer, and polymerization initiator to form a uniform solution;

casting, printing, or spin-coating the uniform solution to form a solution layer of the uniform solution; and exposing the solution layer to ultraviolet light or heat to cure the solution layer.

13. The composition of matter of claim 1, coated as a layer in an adhesive assembly, wherein the layer has a thickness in the range of 1-1000 micrometers.

14. An adhesive assembly comprising the composition of matter of claim 1, wherein the adhesive assembly is a biosensor placed on the substrate comprising a neural interface, living tissue, or skin.

15. The adhesive assembly of claim 14, wherein the biosensor is a multi-electrode array, a nerve cuff electrode, a cortical recording or stimulating electrode, a spinal cord recording or stimulating electrode, a peripheral recording or stimulating electrode, an epidermal electrode, or an epidermal sensor,.

16. A prosthetic or plastic surgical implant comprising the composition of matter of claim 1, wherein the prosthetic or plastic surgical implant substitutes or augments a limb, a hand, a foot, a finger, a toe, a breast, an ear, or a nose.

17. An anatomical model comprising the composition of matter of claim 1, wherein the anatomical model is used to create a tissue phantom, a surgical suture anchor, a stent, a valve, a catheter, or a synthetic tendon.

18. The composition of matter of claim 1, comprising a reversible dry adhesive.

19. A composition of matter useful as an adhesive, comprising:

a bistable adhesive polymer comprising:

one or more polymer backbones;

side-chains attached to each of the polymer backbones;

one or more transition temperatures between a crystalline state and an amorphous state, wherein:

the one or more transition temperatures are such that the polymer transitions from the crystalline state to the amorphous state upon physical contact with a substrate having a temperature higher than the transition temperature of the bistable adhesive polymer; and the polymer adheres or attaches to the substrate with conformity in the amorphous state and can be peeled from the substrate when cooled below the transition temperature of the bistable adhesive polymer to the crystalline state, wherein:

the polymer comprises a copolymer including a combination or mixture of a first component, a second component, a third component, wherein:

the first component has a first transition temperature below the temperature of the substrate, the second component has a second transition temperature greater than the temperature of the substrate, the third component has a storage modulus tailoring a polymer storage modulus of the copolymer such that the storage modulus of the third component and the polymer storage modulus are below 2 MPa at the temperature of the substrate, and the first transition temperature and the second transition temperature are such that the copolymer has the one or more transition temperatures above the first transition temperature but below the temperature of the substrate biological tissue.

20. An on demand adhesive comprising the composition of matter of claim 1, wherein the transition temperature is such that the bistable adhesive polymer adheres to the substrate upon heating to a temperature of 40° C. or higher, and/or wherein the substrate comprises skin or living tissue and the transition temperature of the bistable adhesive polymer is above a temperature of the skin or the living tissue.

* * * * *